(12) United States Patent
Mikos et al.

(10) Patent No.: US 9,283,299 B2
(45) Date of Patent: Mar. 15, 2016

(54) INJECTABLE HYDROGELS

(71) Applicant: WILLIAM MARSH RICE UNIVERSITY, Houston, TX (US)

(72) Inventors: Antonios G. Mikos, Houston, TX (US); F. Kurtis Kasper, Houston, TX (US); Adam K. Ekenseair, Boston, MA (US); Tiffany N. Vo, Houston, TX (US); Kristel W. M. Boere, Utrecht (NL); Tyler J. Touchet, Cypress, TX (US)

(73) Assignee: WILLIAM MARSH RICE UNIVERSITY, Houston, TX (US)

( * ) Notice: Subject to any disclaimer, the term of this patent is extended or adjusted under 35 U.S.C. 154(b) by 0 days.

(21) Appl. No.: 14/298,170

(22) Filed: Jun. 6, 2014

(65) Prior Publication Data

US 2015/0079020 A1    Mar. 19, 2015

Related U.S. Application Data

(63) Continuation-in-part of application No. PCT/US2012/068810, filed on Dec. 10, 2012.

(60) Provisional application No. 61/569,091, filed on Dec. 9, 2011, provisional application No. 61/642,210, filed on May 3, 2012.

(51) Int. Cl.

| | | |
|---|---|---|
| *A61L 27/18* | (2006.01) | |
| *A61K 38/18* | (2006.01) | |
| *A61K 35/28* | (2015.01) | |
| *A61K 9/00* | (2006.01) | |
| *A61K 47/18* | (2006.01) | |
| *A61K 9/06* | (2006.01) | |
| *A61L 27/54* | (2006.01) | |
| *C08L 33/26* | (2006.01) | |
| *A61L 27/52* | (2006.01) | |

(52) U.S. Cl.
CPC ............... *A61L 27/18* (2013.01); *A61K 9/0024* (2013.01); *A61K 9/06* (2013.01); *A61K 35/28* (2013.01); *A61K 38/18* (2013.01); *A61K 47/18* (2013.01); *A61L 27/52* (2013.01); *A61L 27/54* (2013.01); *C08L 33/26* (2013.01); *A61L 2300/252* (2013.01); *A61L 2300/414* (2013.01); *A61L 2300/64* (2013.01); *A61L 2400/06* (2013.01); *A61L 2430/34* (2013.01)

(58) Field of Classification Search
None
See application file for complete search history.

(56) References Cited

U.S. PATENT DOCUMENTS

| | | | | |
|---|---|---|---|---|
| 2008/0255027 A1* | 10/2008 | Moya | ........................ | C07K 1/30 514/1.1 |
| 2009/0111928 A1* | 4/2009 | Mikos et al. | .................. | 524/436 |
| 2009/0123544 A1* | 5/2009 | Liu et al. | ........................ | 424/484 |
| 2011/0097406 A1* | 4/2011 | Bryant et al. | ................. | 424/486 |

* cited by examiner

*Primary Examiner* — Carlos Azpuru
*Assistant Examiner* — Casey Hagopian
(74) *Attorney, Agent, or Firm* — Reed Smith LLP; Robert R. Riddle; Matthew S. Gibson

(57) ABSTRACT

The present disclosure generally relates to injectable compositions. More particularly, the present disclosure relates to injectable, thermogelling hydrogels and associated methods. In one embodiment, the present disclosure provides for a composition comprising a poly(N-isopropylacrylamide)-based macromer and a polyamidoamine-based macromer.

16 Claims, 32 Drawing Sheets
(5 of 32 Drawing Sheet(s) Filed in Color)

x. dimethyl-γ-butyrolactone acrylate (LSCT ↓)

y. N-isopropylacrylamide (NiPAAm) (LCST = 32°)

z. Acrylic Acid (AA) (LCST ↑)

m. Glycidyl Methacrylate (GMA) (LSCT ↓)

\* Effect of TGM wt% significant, p<0.05; # Effect of PAMAM length significant on same TGM; & Effect of DBA mol content significant with same PAMAM

| PAMAM | Feed Ratio, r | $M_n$ (NMR) |
|---|---|---|
| P-1 | 0.6 | 675 |
| P-2 | 0.78 | 1890 |
| P-3 | 0.85 | 3000 |

| Factor | PAMAM MW | Wt % TGM | Amine:Epoxy Mol Ratio | Prep Time |
|---|---|---|---|---|
| # Levels per Factor | 3 | 3 | 3 | 3 |
| Levels | 800, 1800, 2600 Da | 10, 15, 20 wt % | 0.5:1, 1:1, 1.5:1 | 10, 20, 30 min |
| Total Hydrogel Formulations Tested | | | 81 | |

10 wt % TGM, 0 min Prep Time

Accelerated Degradation in PBS pH=10 at 37°C

Accelerated Degradation in PBS pH=10 at 37°C

FIG. 38
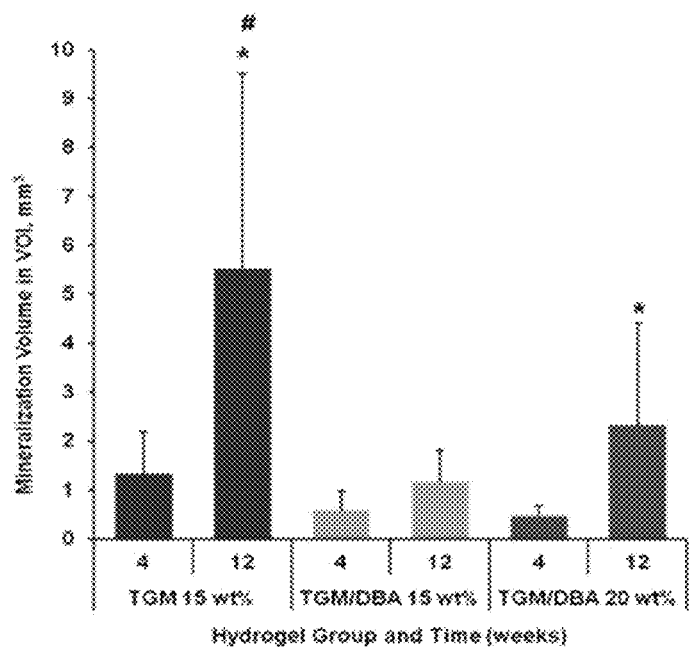
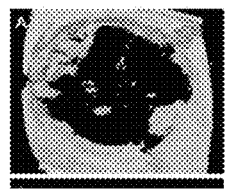 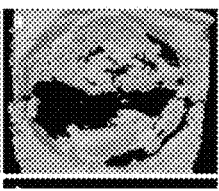 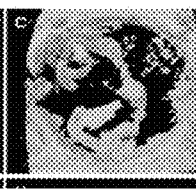 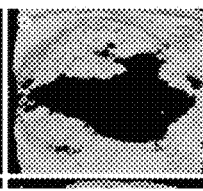 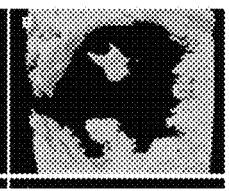
FIG. 39A    FIG. 39B    FIG. 39C    FIG. 39D    FIG. 39E
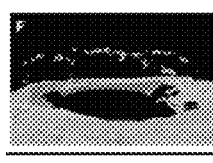 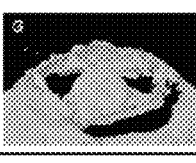 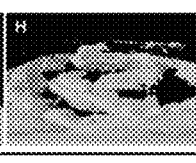 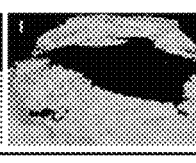 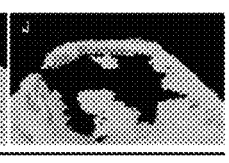
FIG. 39F    FIG. 39G    FIG. 39H    FIG. 39I    FIG. 39J
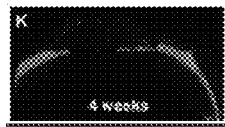   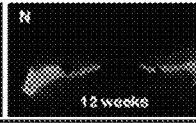 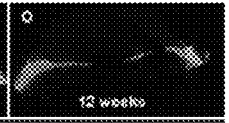
FIG. 39K    FIG. 39L    FIG. 39M    FIG. 39N    FIG. 39O FIG. 40A
FIG. 40B
FIG. 40C
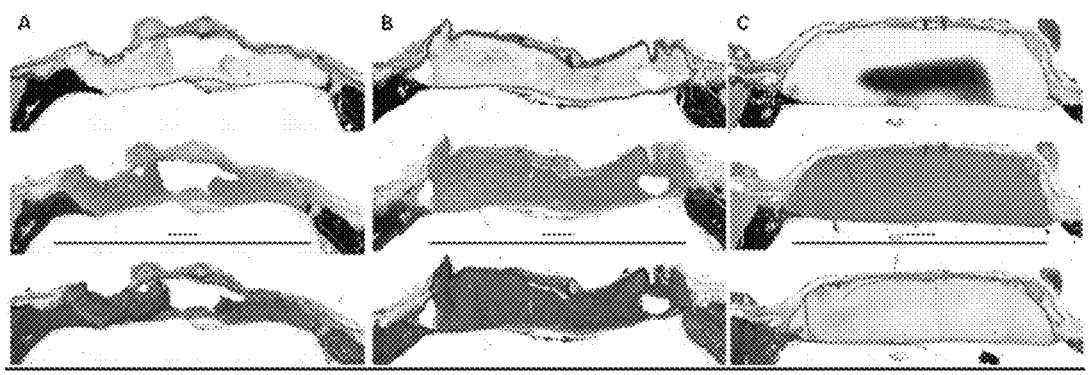
FIG. 40D
FIG. 40E
FIG. 40F
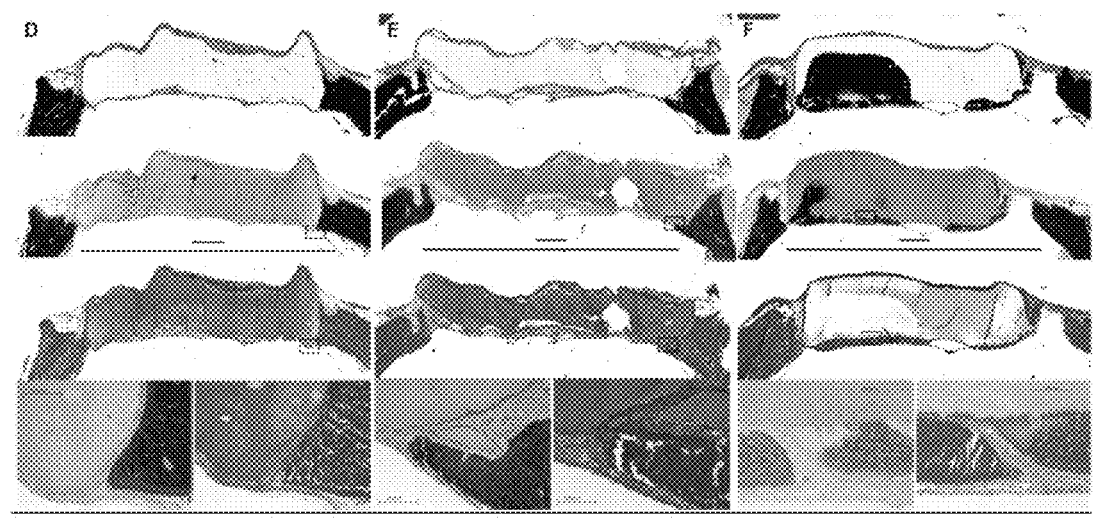

INJECTABLE HYDROGELS

CROSS-REFERENCE TO RELATED APPLICATIONS

This application is a continuation-in-part of PCT/US2012/068810 filed Dec. 10, 2012 which claims priority to U.S. Provisional Patent Application Ser. No. 61/569,091 filed Dec. 9, 2011 and U.S. Provisional Patent Application Ser. No. 61/642,210 filed May 3, 2012, both of which are incorporated herein by reference.

STATEMENT REGARDING FEDERALLY SPONSORED RESEARCH OR DEVELOPMENT

This invention was made with government support under Grant No. R01 DE17441 awarded by National Institute of Health. The government has certain rights in the invention.

BACKGROUND

The majority of effort in tissue regeneration research has been focused on implantable scaffolds. However, there are many applications that may be better served with injectable, in situ forming materials capable of co-delivering cells and growth factors to optimize tissue regeneration.

In addition, current tissue engineering strategies remain limited in providing functional and aesthetic reconstruction for complex craniofacial trauma.

It is therefore desirable to develop an injectable scaffold system capable of delivering in situ forming materials capable of co-delivering cells and growth factors to optimize tissue regeneration. It would also be desirable to develop a tissue engineering strategy that is especially suited for providing functional and aesthetic reconstruction for complex craniofacial trauma.

SUMMARY

The present disclosure generally relates to injectable compositions. More particularly, the present disclosure relates to injectable, thermogelling hydrogels and associated methods.

In one embodiment, the present disclosure provides for a composition comprising a poly(N-isopropylacrylamide)-based macromer and a polyamidoamine-based macromer.

In another embodiment, the present disclosure provides for a method comprising providing a composition comprising a polyamidoamine-based macromer and a poly(N-isopropylacrylamide)-based macromer; and allowing the composition to crosslink.

In another embodiment, the present disclosure provides for a method comprising providing a composition comprising a polyamidoamine-based macromer and a poly(N-isopropylacrylamide)-based macromer; injecting the composition into a defect in a mammal; and allowing the composition to solidify, wherein the composition solidifies at the site of the defect.

In another embodiment, the present disclosure provides for an injectable scaffold comprising a poly(N-isopropylacrylamide)-based macromer and a polyamidoamine-based macromer.

In another embodiment, the present disclosure provides for a hydrogel composition comprising a polyamidoamine-based macromer.

In another embodiment, the present disclosure provides for a hydrogel composition comprising a poly(N-isopropylacrylamide)-based macromer.

The features and advantages of the present disclosure will be apparent to those skilled in the art. While numerous changes may be made by those skilled in the art, such changes are within the spirit of the invention.

DRAWINGS

The patent or application file contains at least one drawing executed in color. Copies of this patent or patent application publication with color drawing(s) will be provided by the Office upon request and payment of the necessary fee. Some specific example embodiments of the disclosure may be understood by referring, in part, to the following description and the accompanying drawings.

Figure 3A:
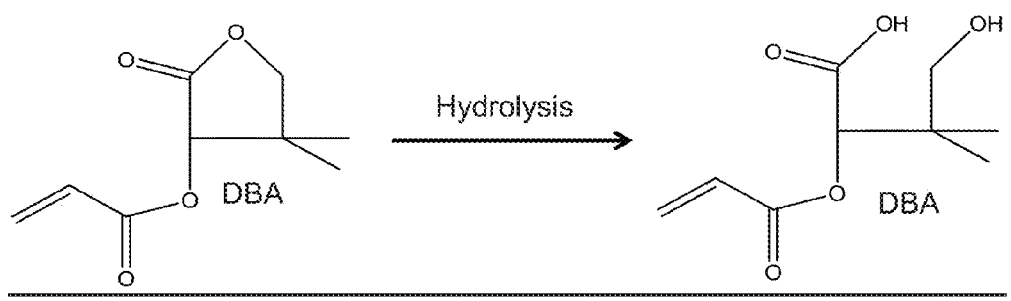
Figure 3B:
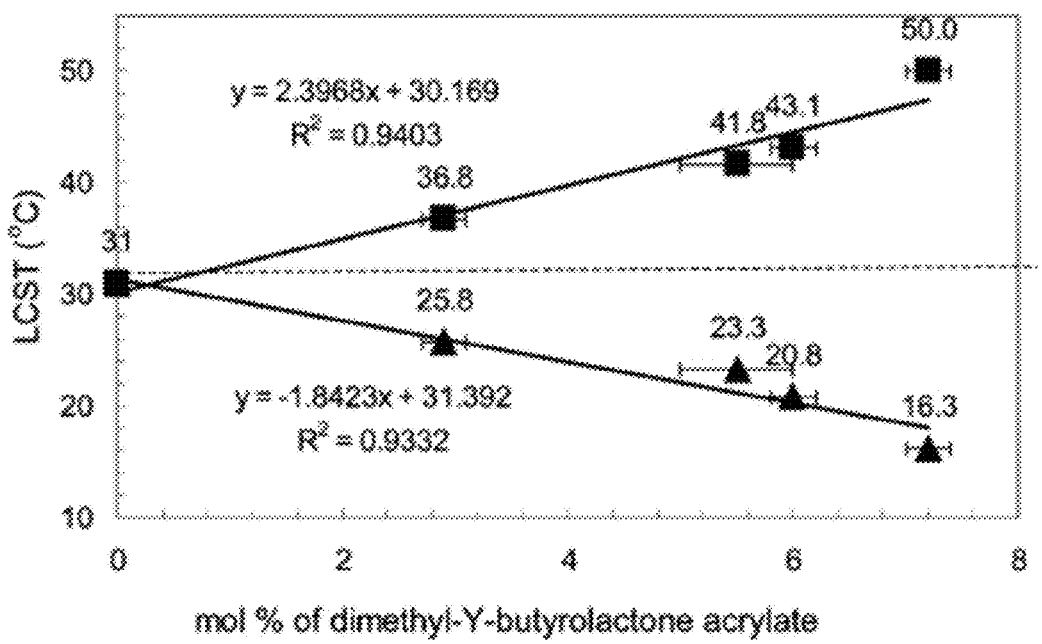
Figure 3C:
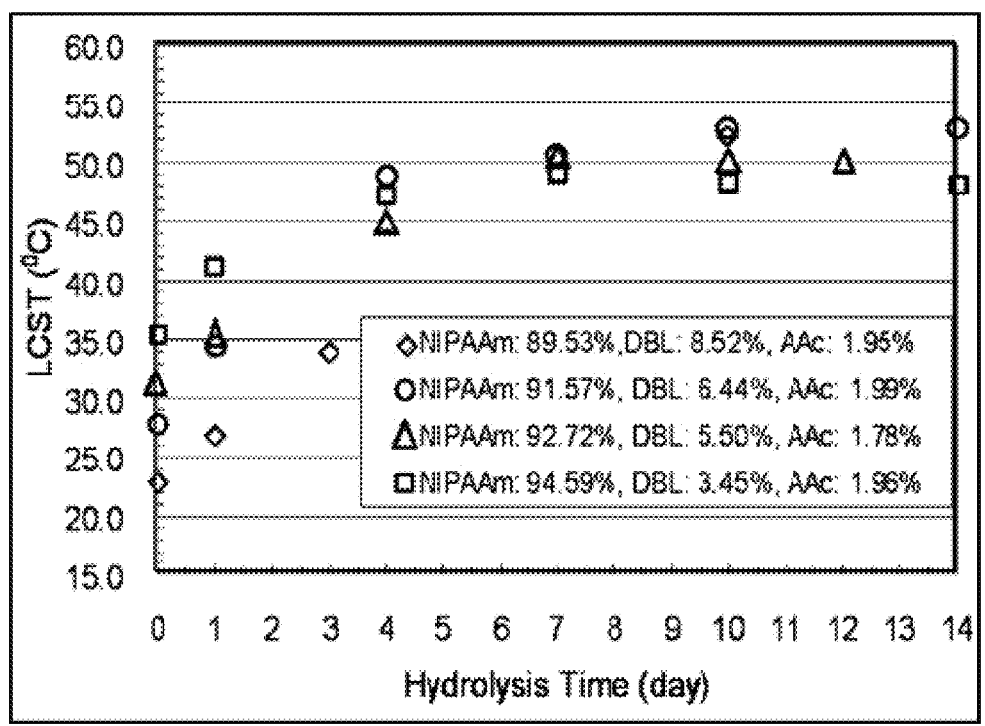

FIGS. 3A, 3B, and 3C illustrate LCST modulation. FIG. 3A illustrates the hydrolysis of DBA. FIG. 3B illustrates initial (▲) and final (■) LCST of polymer with different DBA mol content in complete hydrolysis conditions (pH=10 at 70° C.). FIG. 3C illustrates LCST change as a function of time of polymers with different DBA mol content during degradation (pH=7.4 at 70° C.).

Figure 4:
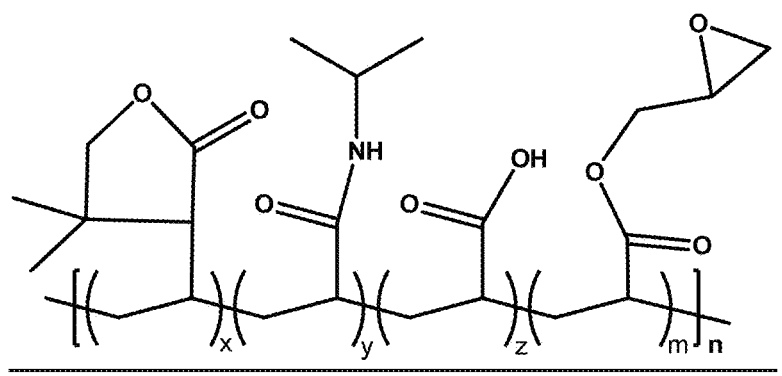

FIG. 4 is a drawing that illustrates one example of the basic structure of a thermogelling macromer of the present disclosure.

Figure 5:
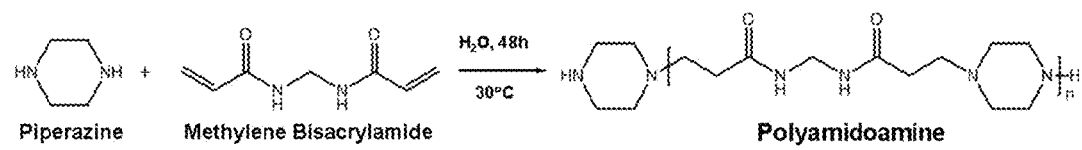

FIG. 5 is illustrating synthesis of polyamidoamine, wherein n may be greater than or equal to 1.

Figure 6:
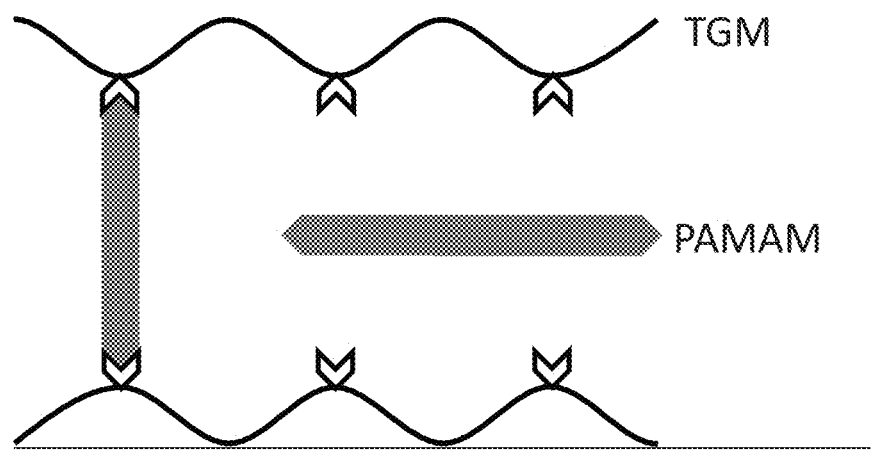

FIG. 6 is a drawing that illustrates how hydrogels may form in TGM containing GMA with a PAMAM crosslinker.

Figure 7:
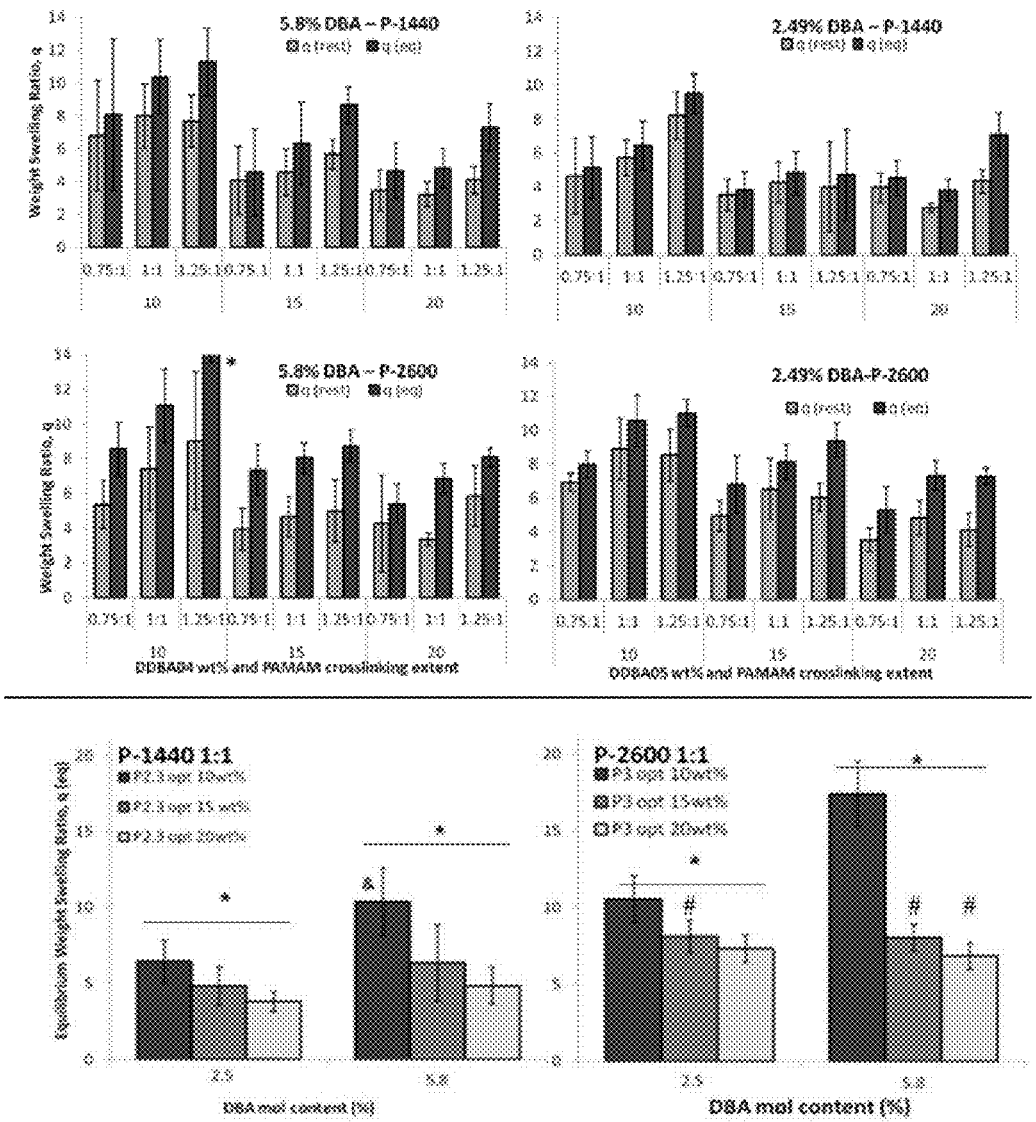

FIG. 7 is a drawing that illustrates the results of a factorial study design.

Figure 8A:
Figure 8B:
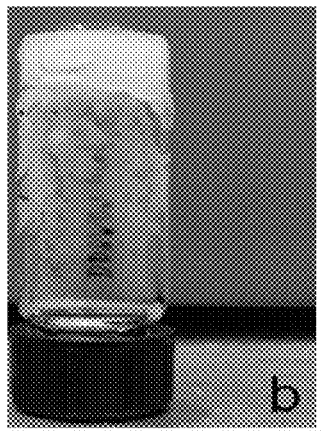
Figure 8C:
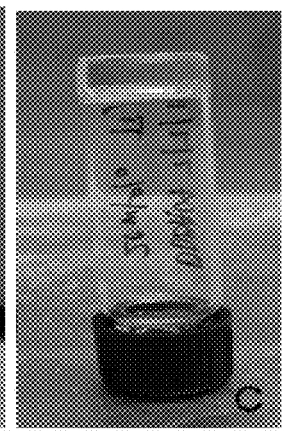

FIGS. 8A, 8B, and 8C illustrate gels using thermoresponsive, chemically crosslinked macromers. TGM without GMA undergoes syneresis without PAMAM (left vial) and remains liquid with PAMAM (right vial) after 1 day (FIG. 8A). TGM with GMA and PAMAM thermogelled after 1 minute (FIG. 8B) and fully formed after 30 minutes (FIG. 8C).

Figure 9:
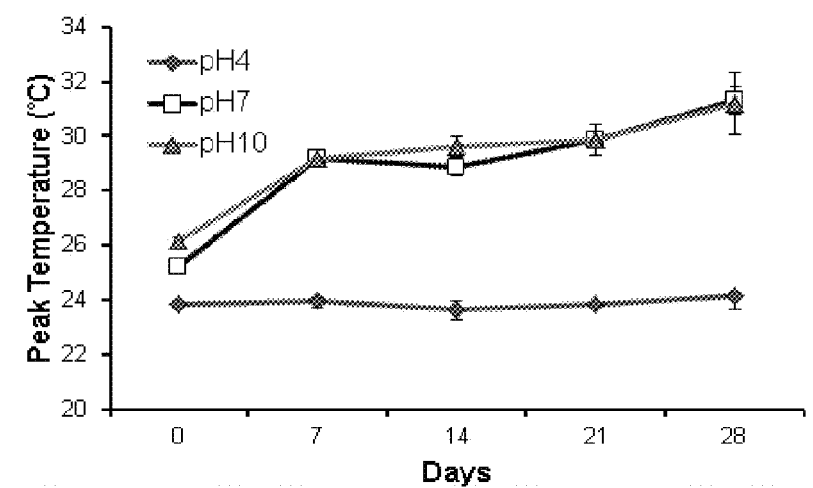
Figure 10:
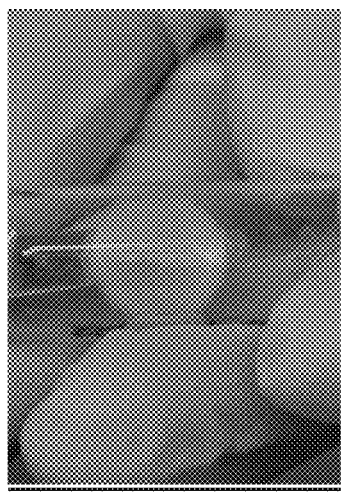

FIG. 9 illustrates degradation studies. Hydrolysis-dependent peak LCST of TGM without GMA over 28 days FIG. 10 is an image of a P-BA gel.

Figure 11:
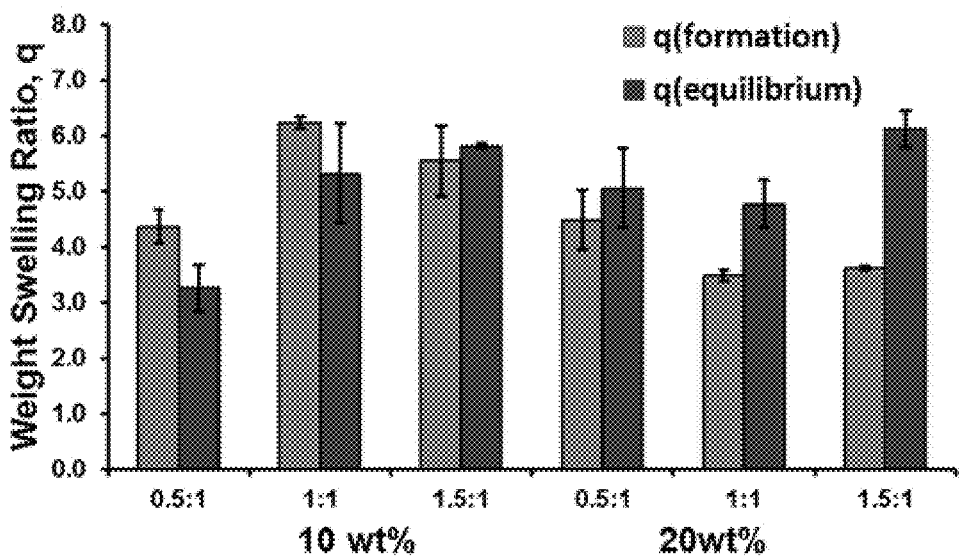

FIG. 11 illustrates swelling ratios of P(NiPAAm-co-GMA). Swelling ratios of P(NiPAAm-co-GMA) at 10 and 20 wt % in PBS with P-2.6 kDa at varying crosslinker:polymer functionality ratios.

Figure 12:
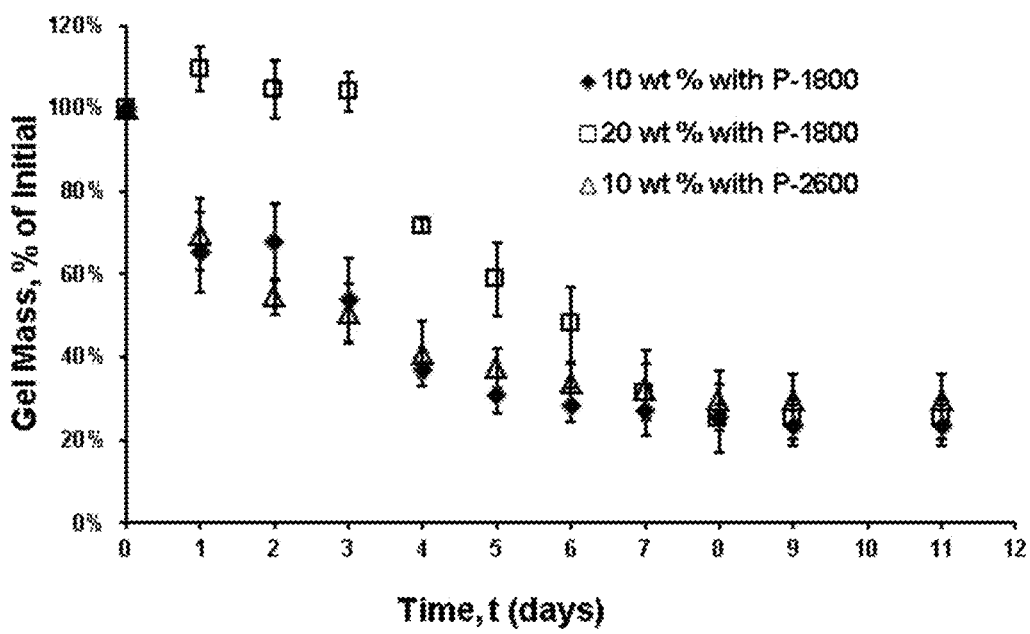

FIG. 12 illustrates degradation rates of formulations with varying PAMAM molecular weight. Accelerated degradation of P(NiPAAmco-GMA) at 10 and 20 wt % in PBS pH 10 with P-1800 and at 10 wt % with P-2600.

Figure 13:
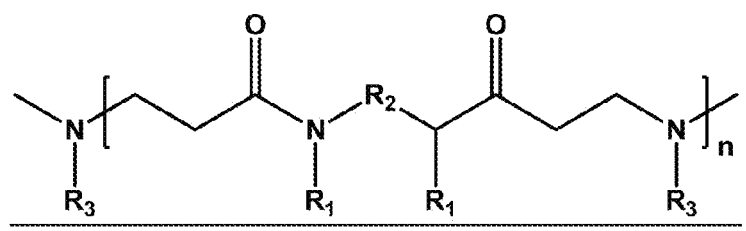

FIG. 13 illustrates a polyamidoamine.

Figure 14A:
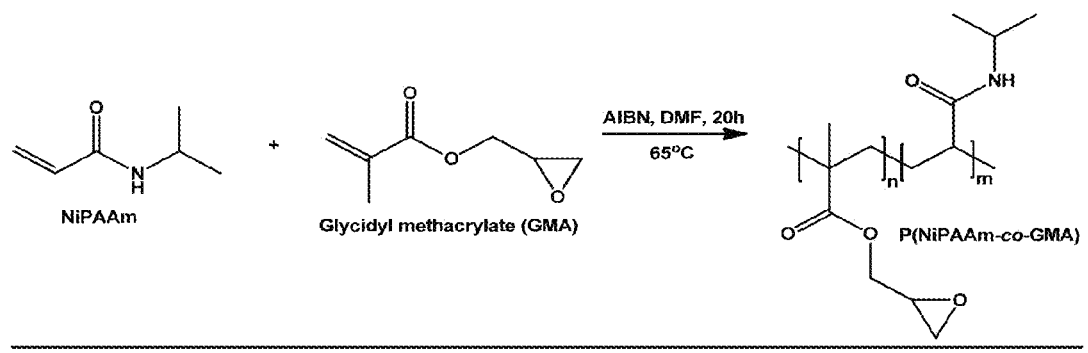
Figure 14B:
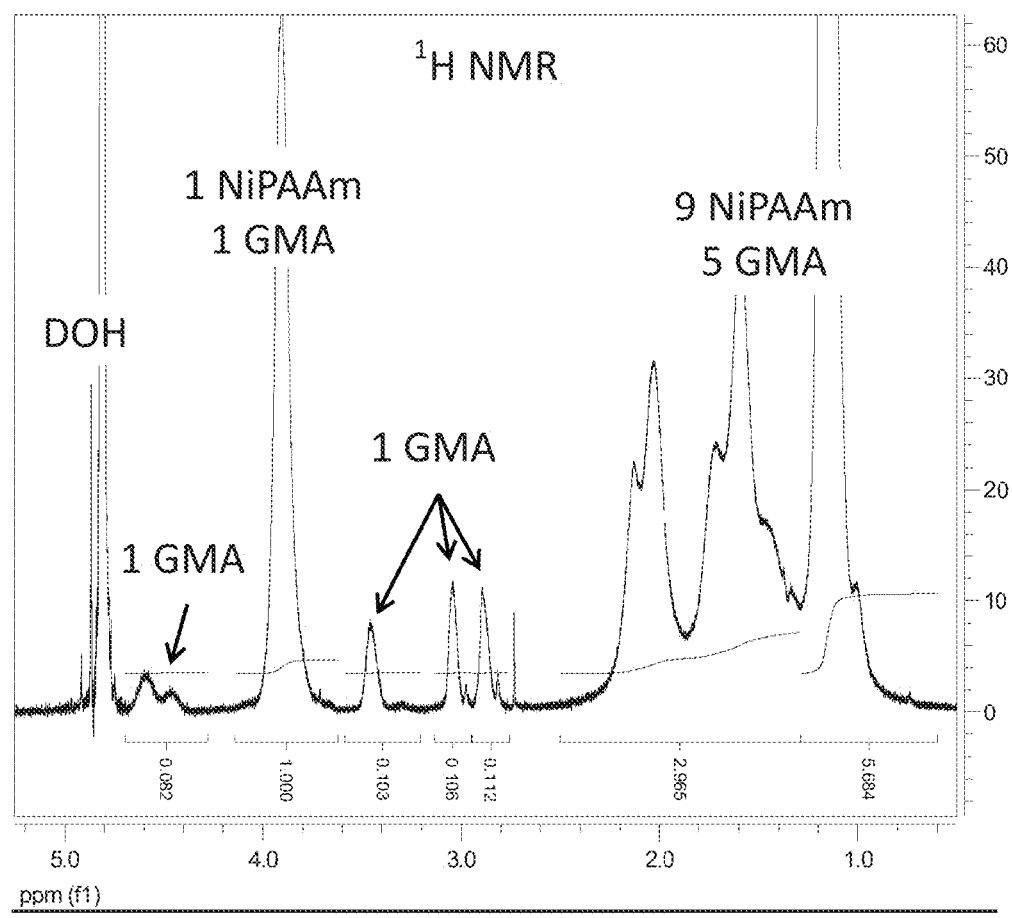

FIGS. 14A and 14B illustrate the synthesis of a thermogelling macromer (TGM).

Figure 15:
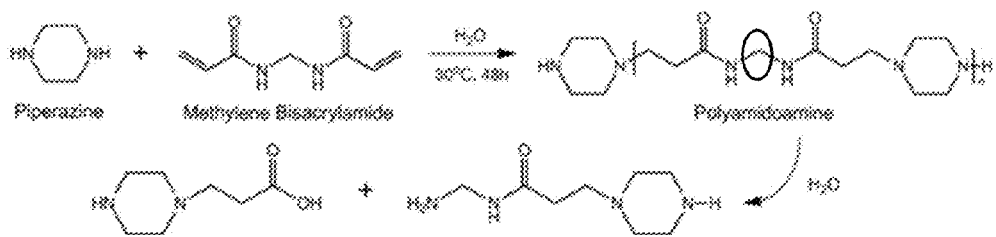
Figure 15:
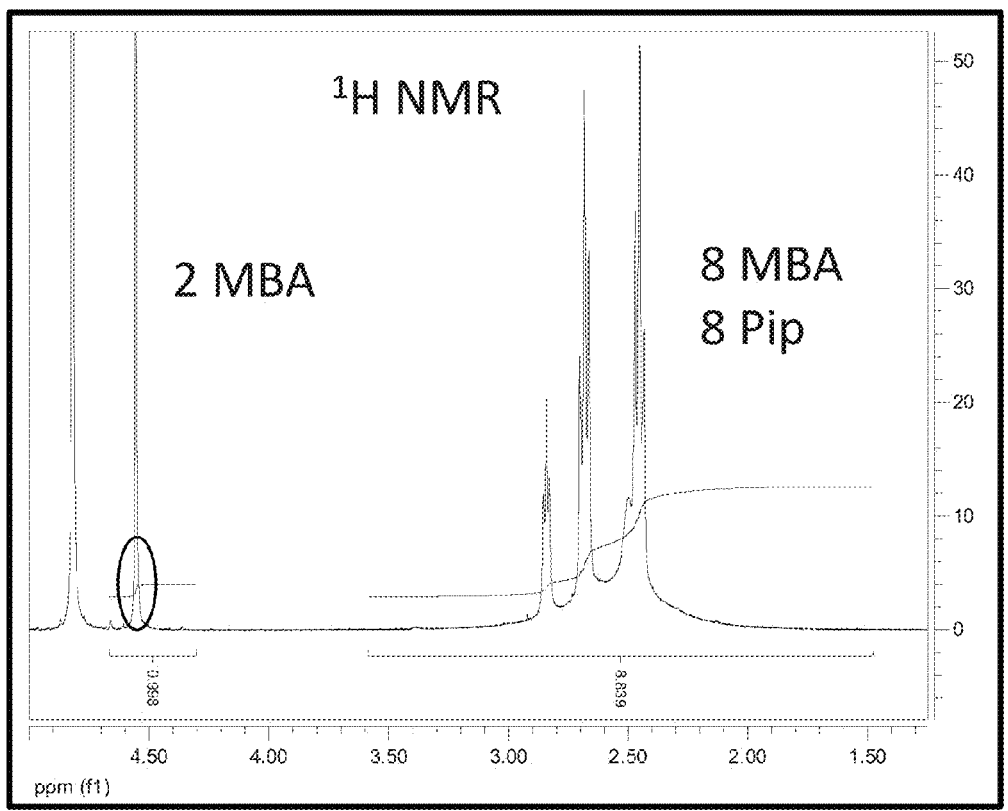

FIG. 15 illustrates the synthesis of a polyamidoamine (PAMAM).

Figure 16:
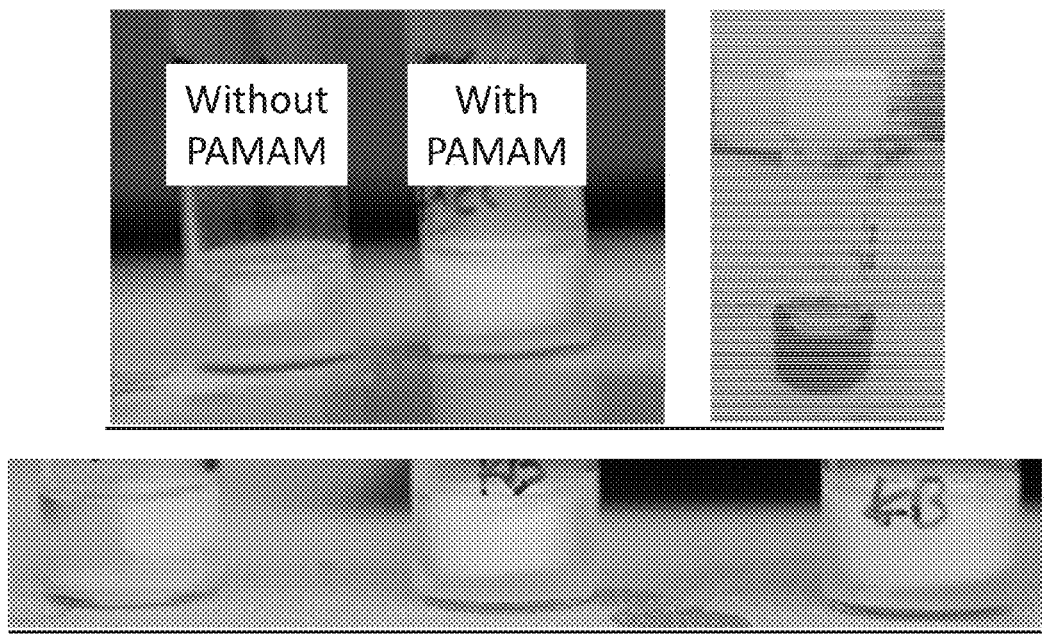

FIG. 16 illustrates a TGM/PAMAM gelation factorial study.

Figure 17:
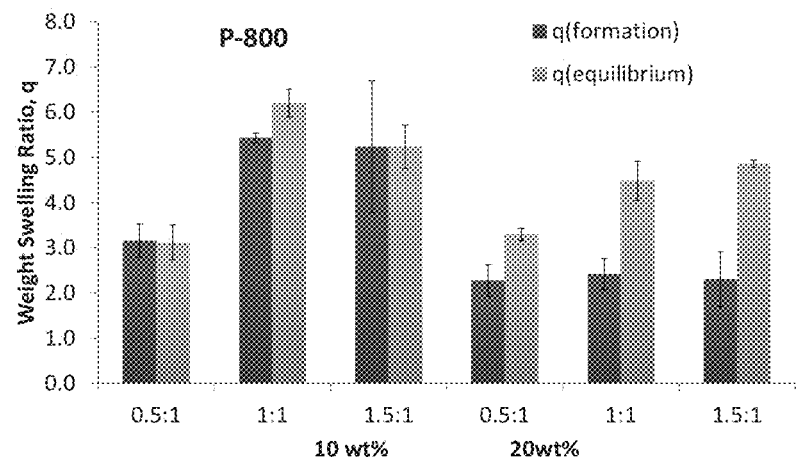
Figure 17:
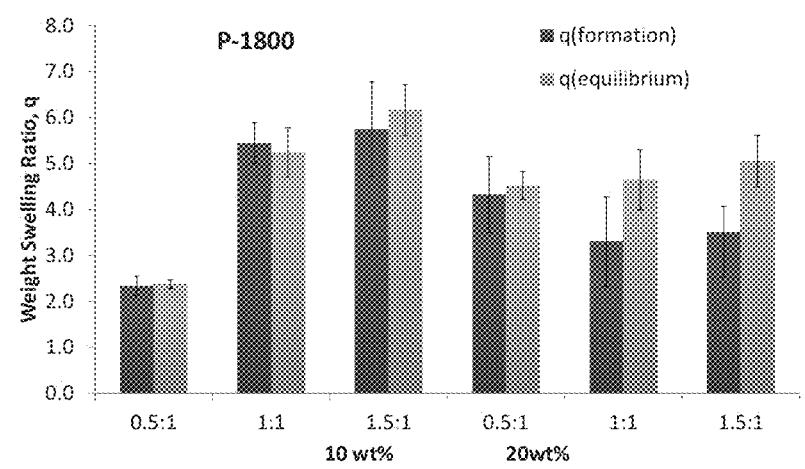
Figure 17:
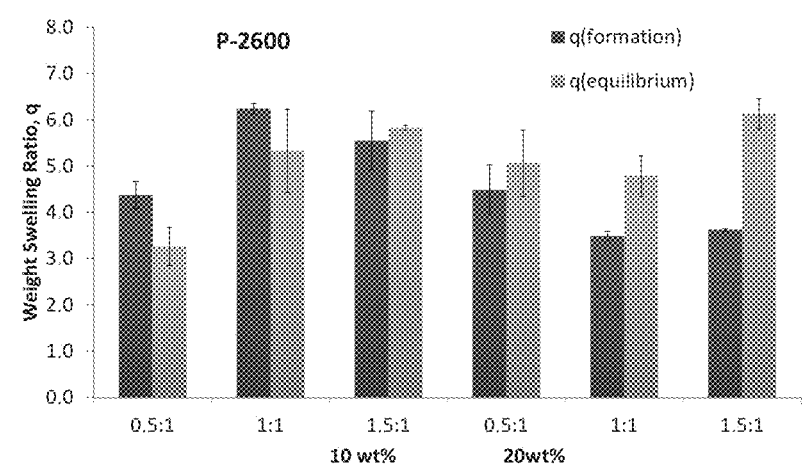

FIG. 17 illustrates gelation and equilibrium swelling.

Figure 18:
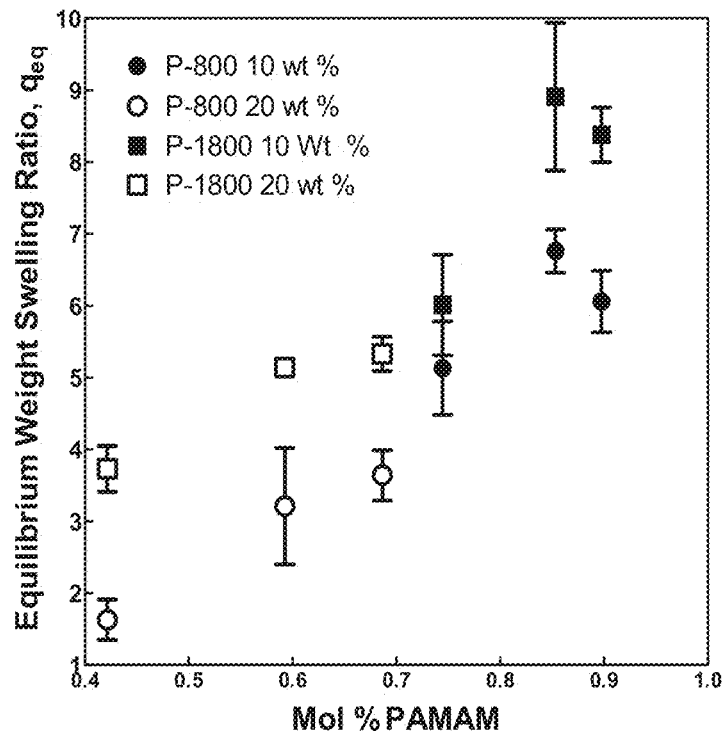
Figure 18:
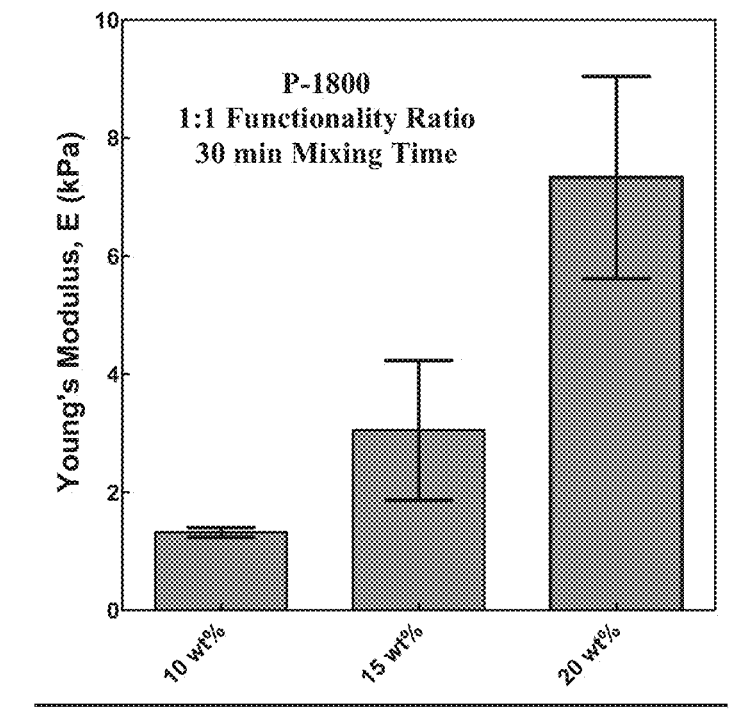

FIG. 18 illustrates factorial study results.

Figure 19:
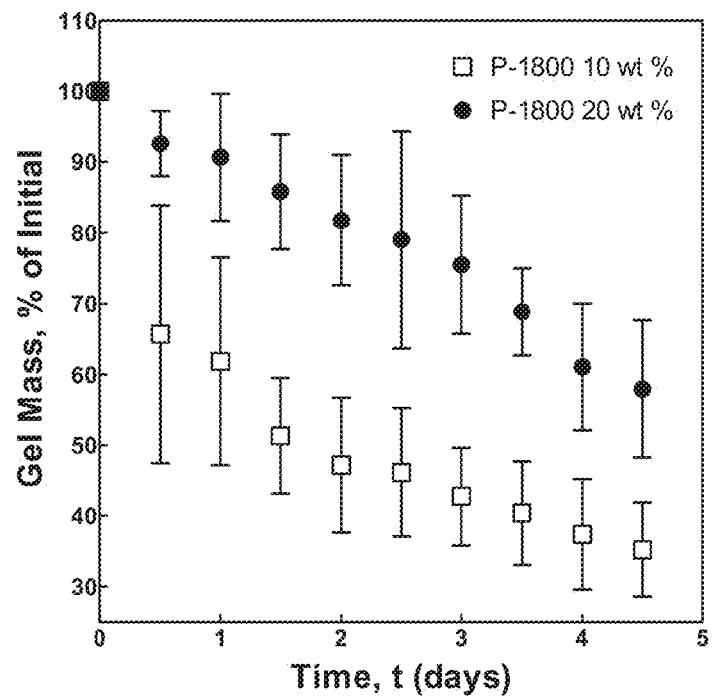
Figure 19:
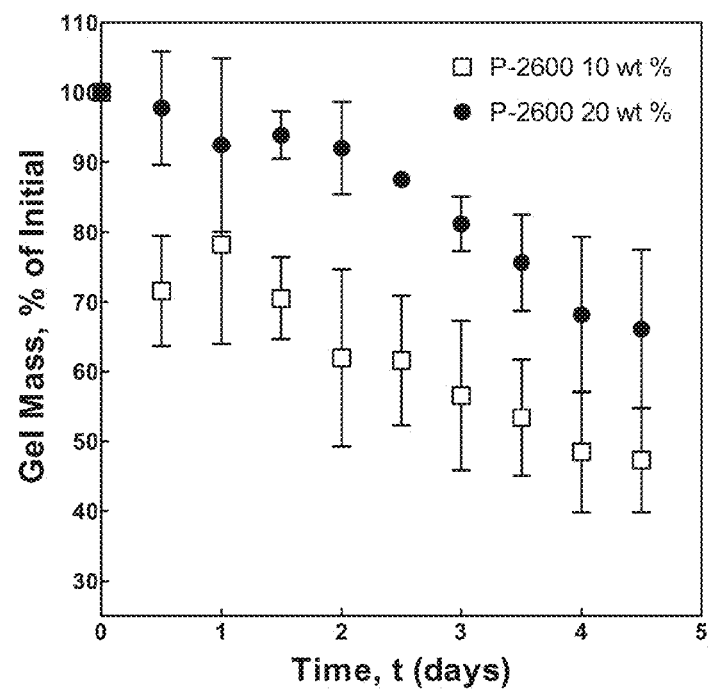

FIG. 19 illustrates PAMAM degradation.

Figure 20:
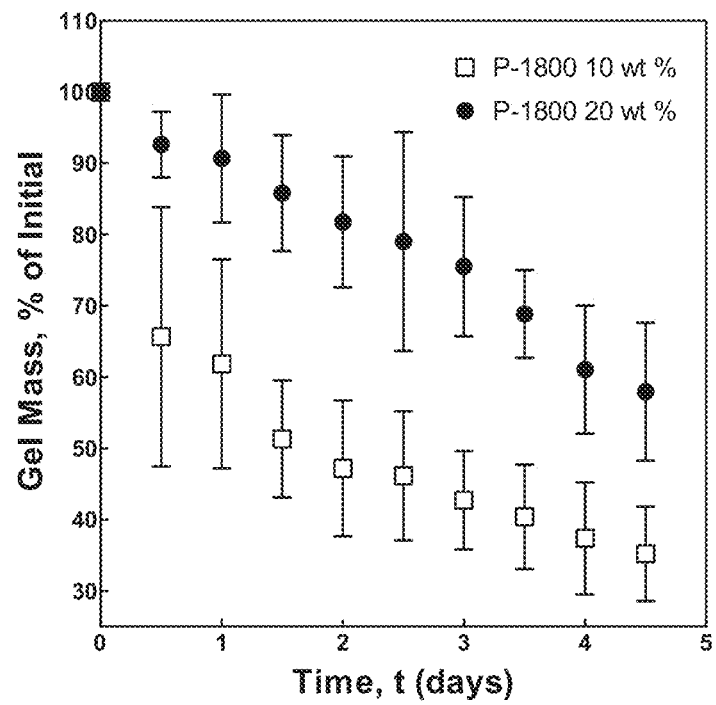
Figure 20:
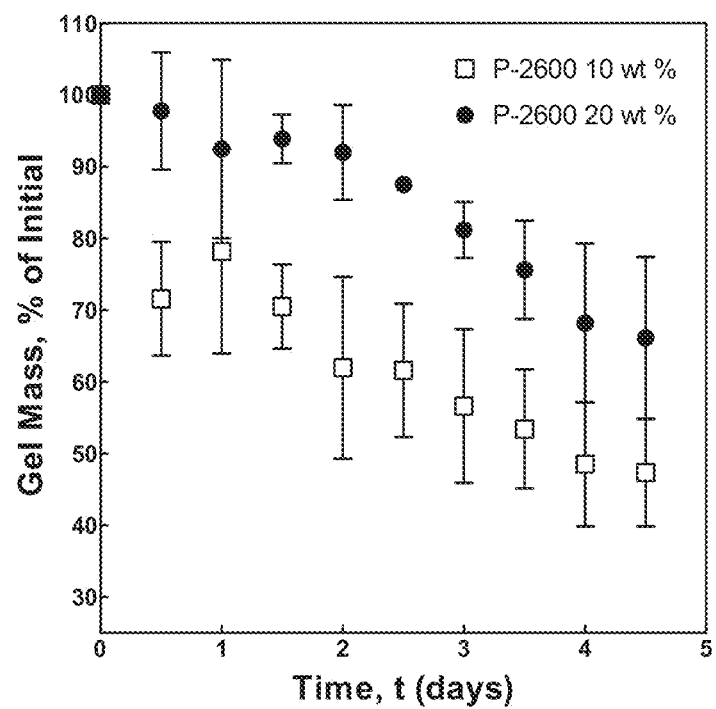

FIG. 20 illustrates PAMAM degradation.

Figure 21:
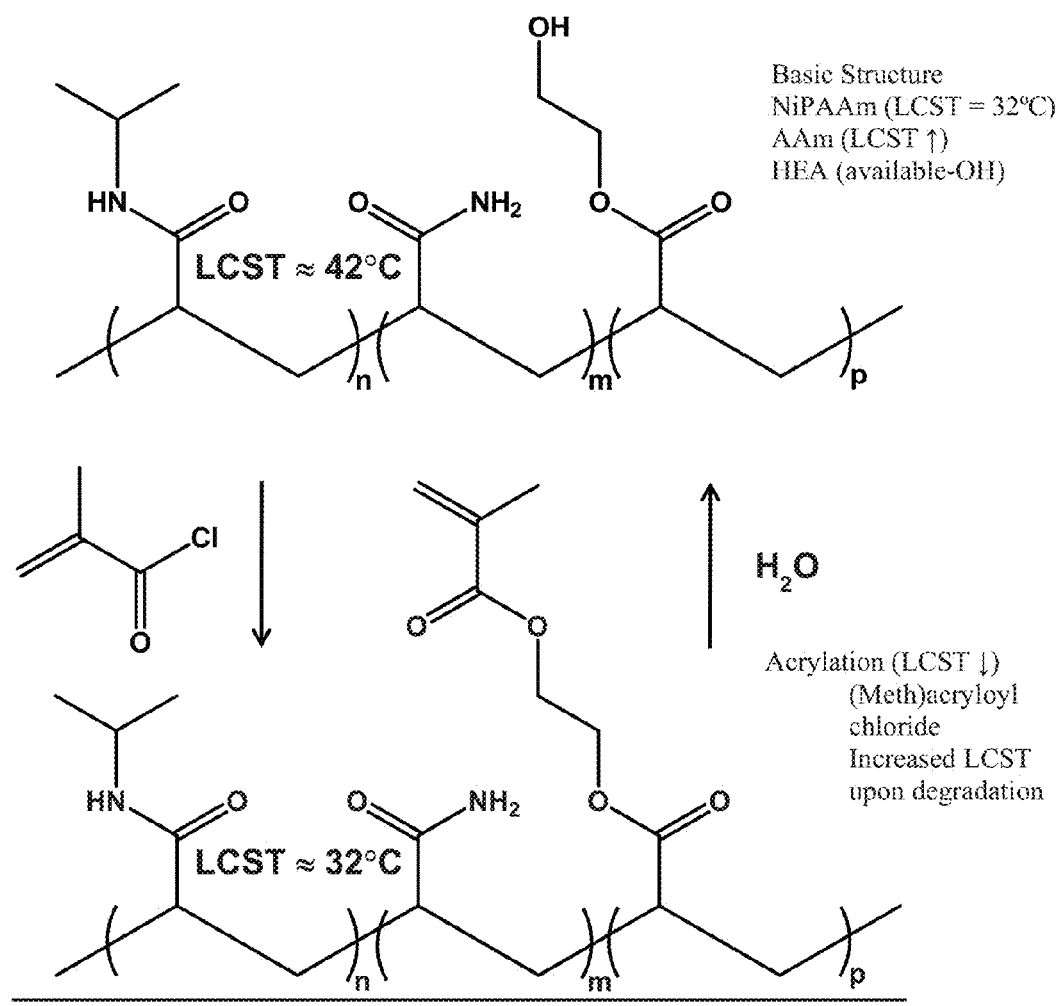

FIG. 21 illustrates a PAMA-BA system.

Figure 22:
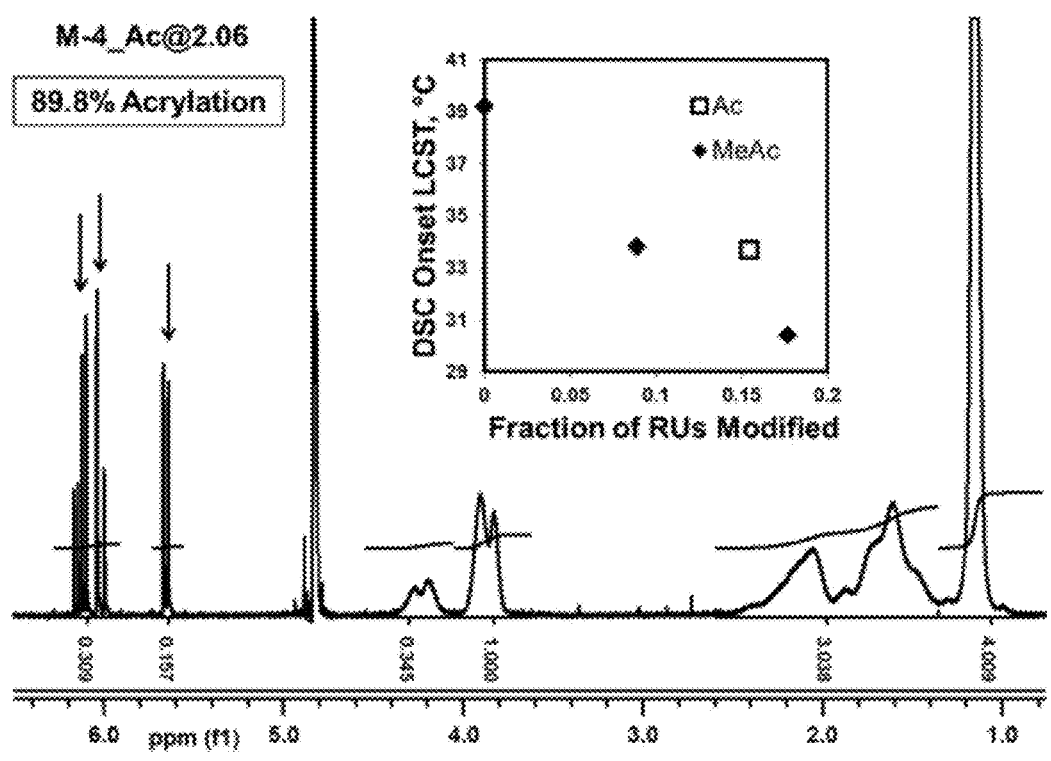

FIG. 22 illustrates the results of degree of modification.

Figure 23:
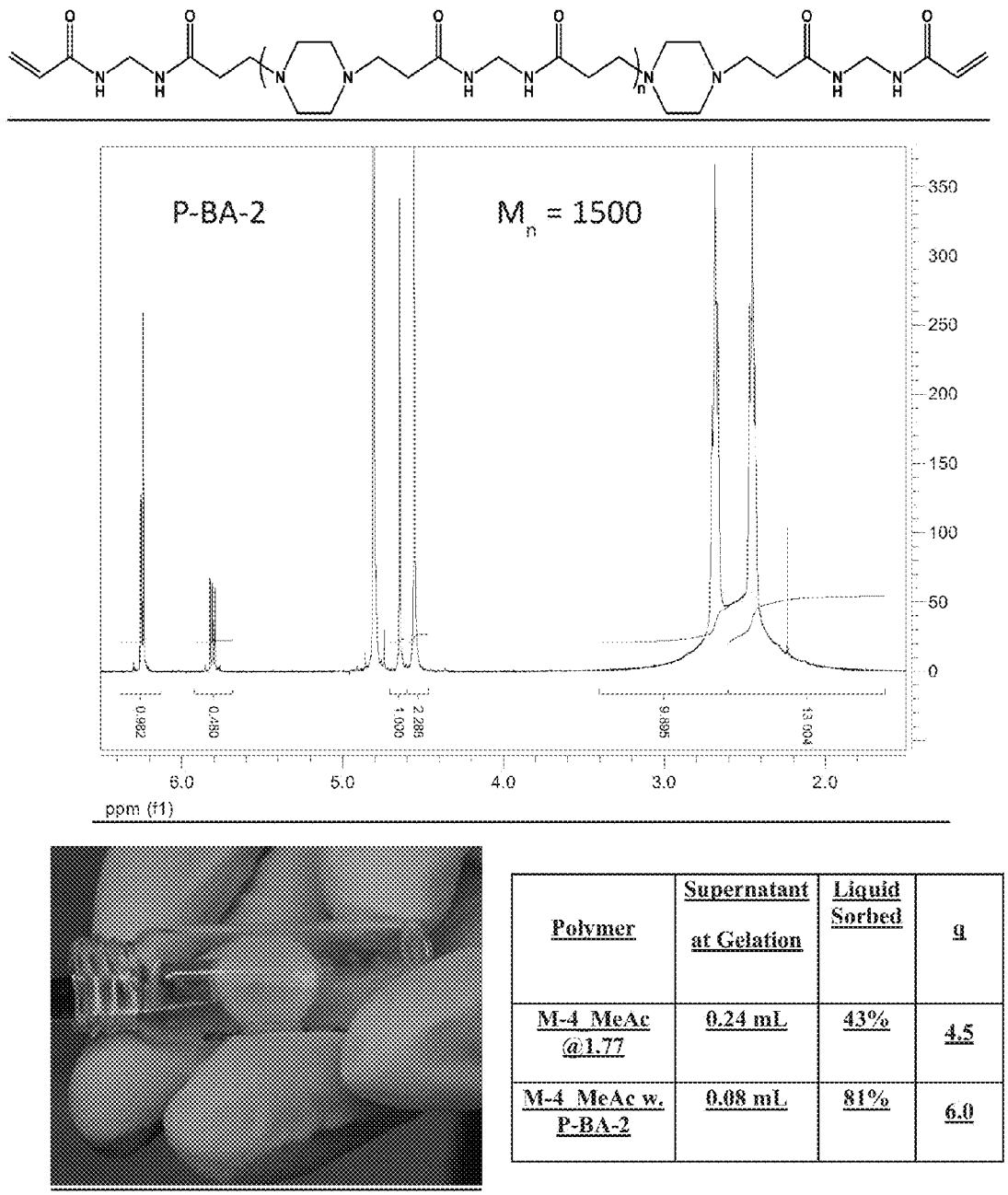

FIG. 23 illustrates PAMAM-BA.

Figure 24:
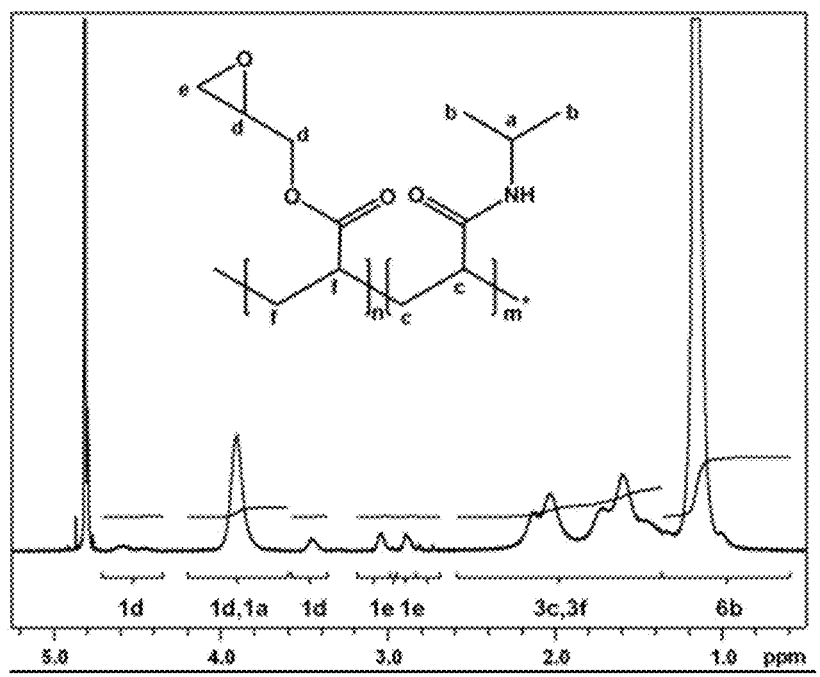

FIG. 24 illustrates $^1$H NMR spectra of p(NiPAAm-co-GMA) with proton peak locations identified.

Figure 25:
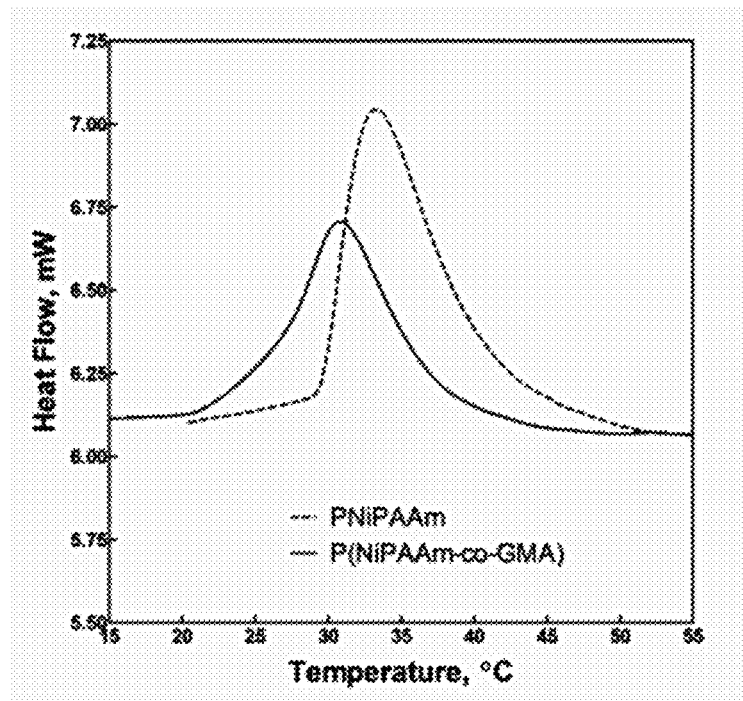

FIG. 25 illustrates DSC thermograms for pNiPAAm and p(NiPAAm-co-GMA) at 10 wt % polymer in pH 7.4 PBS solutions.

Figure 26:
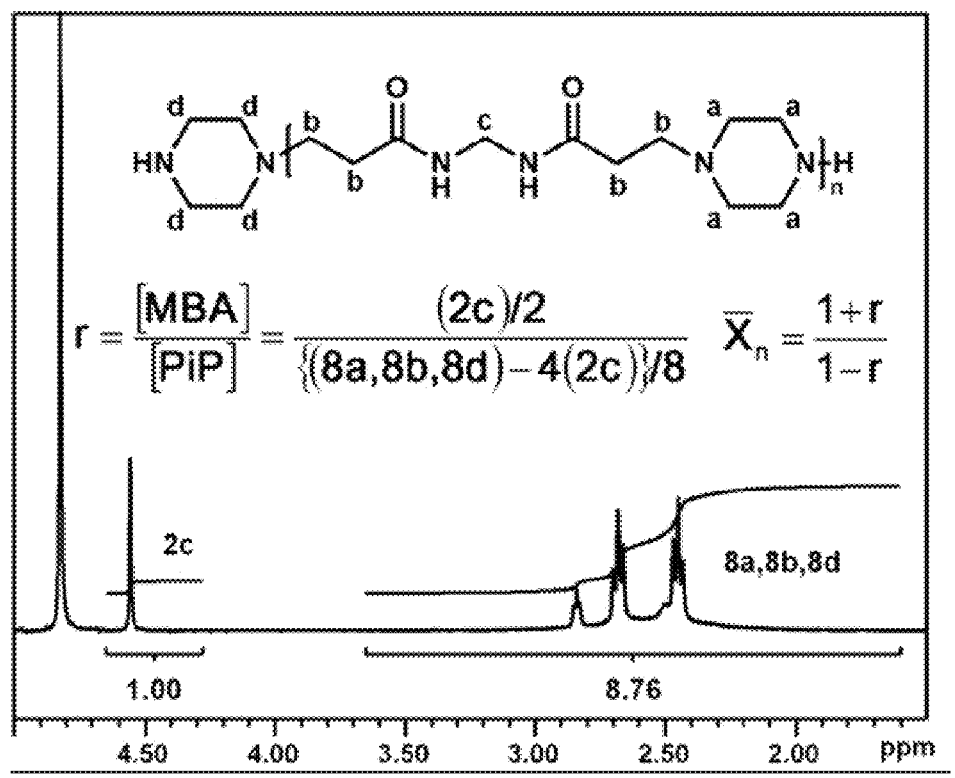

FIG. 26 shows $^1$H NMR spectra of PAMAM with proton peak locations identified and equations utilized to calculate an experimental average molecular weight based on peak intensities displayed.

Figure 27:
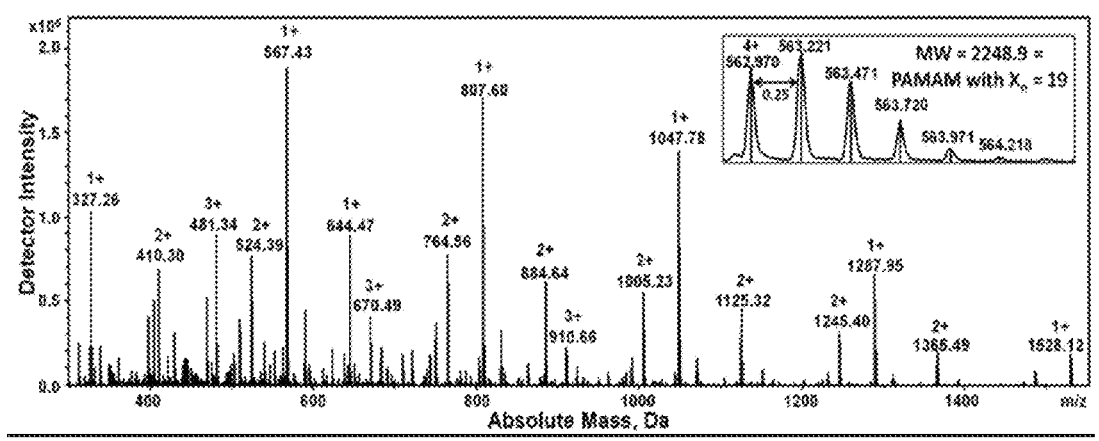

FIG. 27 shows raw microTOF mass spectroscopy data for purified/dried PAMAM crosslinker showing molecular weights and charge states for some of the largest peaks, with a close-up view of a single peak family (insert).

Figure 28:
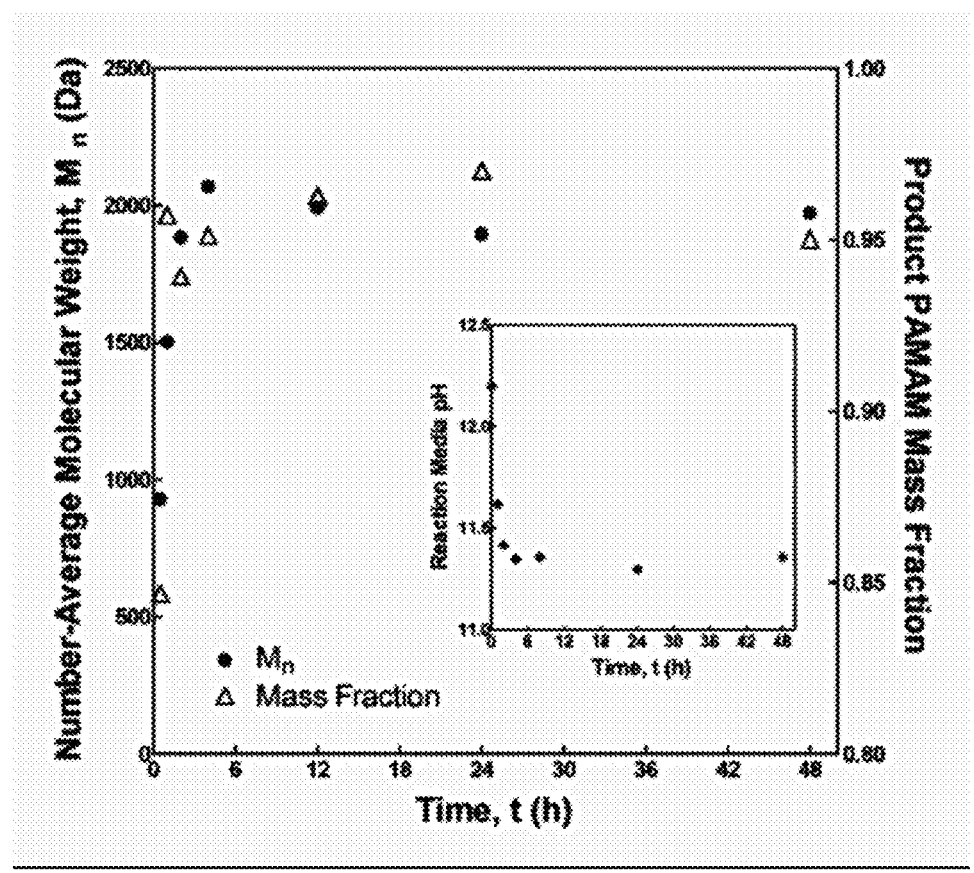

FIG. 28 shows desired PAMAM diamine product $M_n$, and weight fraction of the total reaction products, as determined by microTOF mass spectroscopy, and reaction media pH (insert) over the course of the synthesis reaction.

Figure 29:
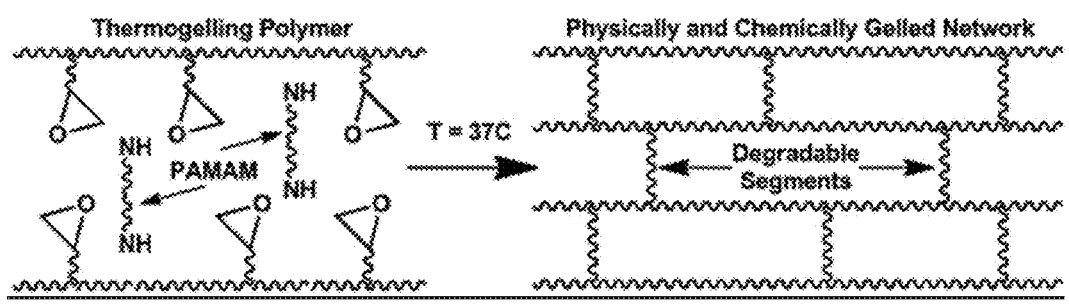

FIG. 29 shows a schematic representation of the hydrogel epoxy crosslinking reaction.

Figure 30:
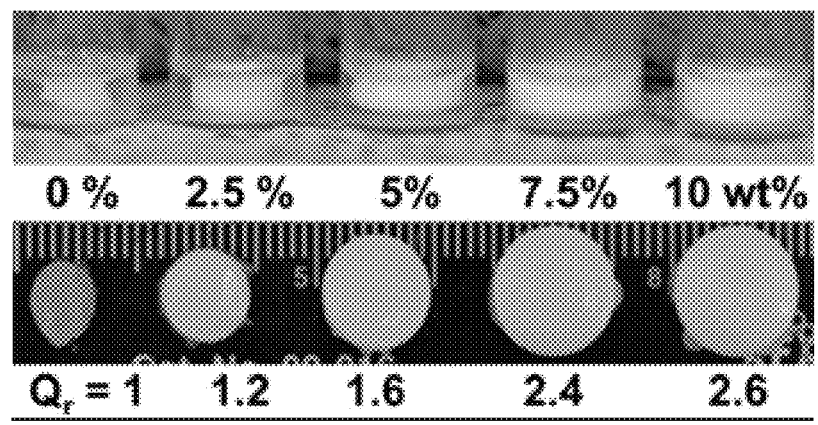

FIG. 30 shows hydrogel formation and syneresis with 10 wt % TGM and varying PAMAM content (0-10 wt %) with volume swelling ratio relative to 0% PAMAM, $Q_r$, shown.

Figure 31:
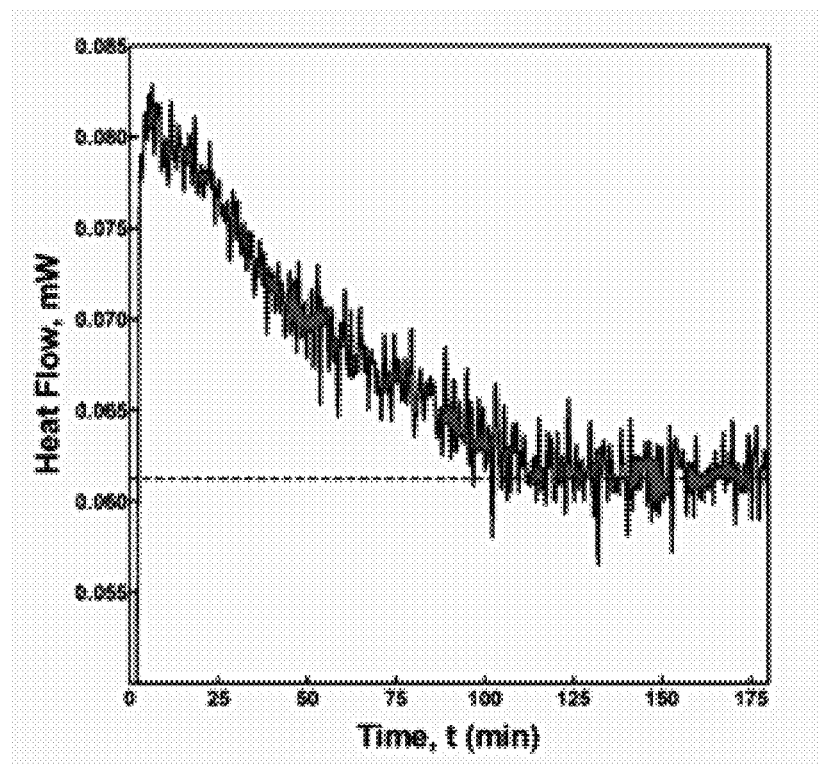

FIG. 31 shows a DSC thermogram monitoring heat flow over time during the epoxy crosslinking reaction of a 10 wt % TGM and 7 wt % PAMAM solution in pH 7.4 PBS.

Figure 32:
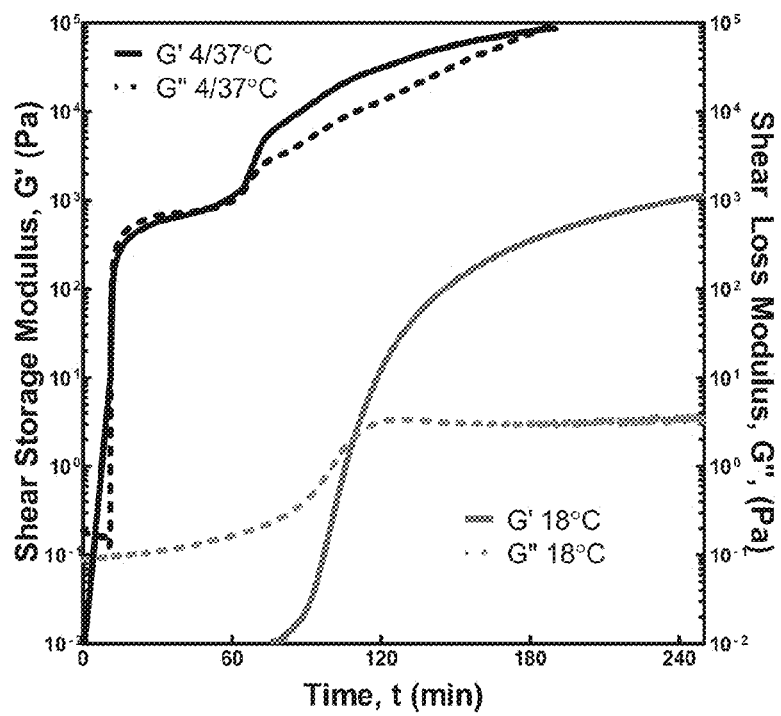

FIG. 32 shows oscillatory rheology traces showing shear storage, G', and loss, G", moduli for an injectable hydrogel solution with 7 wt % PAMAM and 10 wt % TGM in pH 7.4 PBS either held at 18° C. for 4 h or held first at 4° C. for 10 min and then at 37° C. for 3 h.

Figure 33:
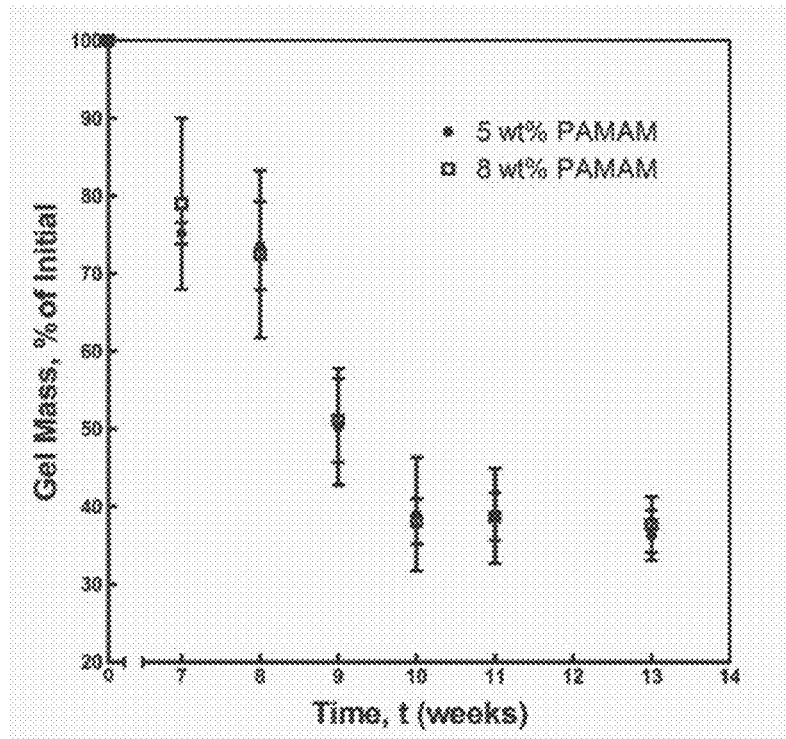

FIG. 33 shows long-term mass loss due to PAMAM degradation in pH 7.4 PBS of hydrogels with 10 wt % TGM and either 5 or 8 wt % PAMAM.

Figure 34:
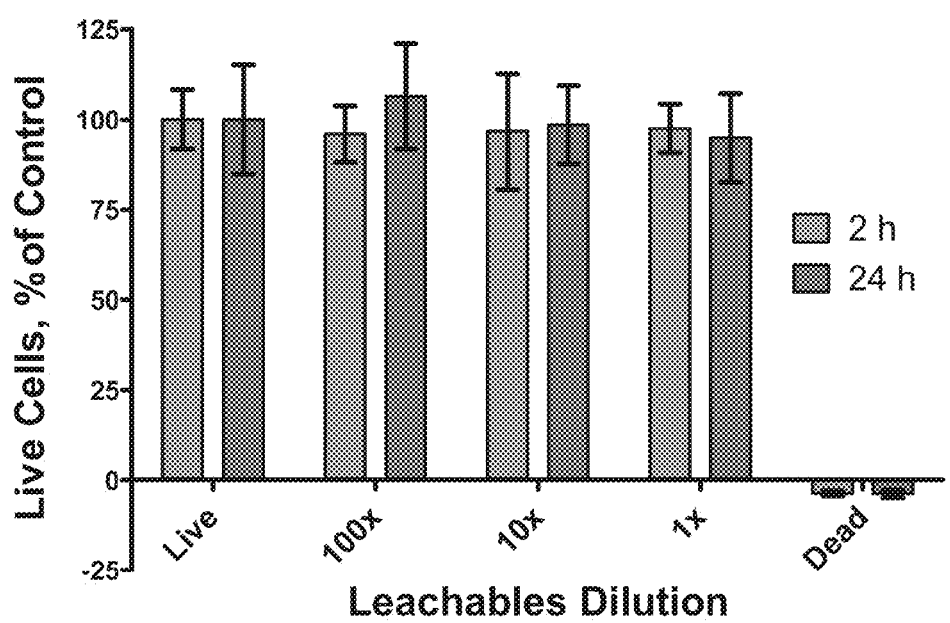

FIG. 34 shows viability of rat fibroblasts exposed to soluble leachables from hydrogels with 7 wt % PAMAM and 10 wt % TGM in 1, 10, and 100× dilutions over 2 and 24 h relative to the live control as determined by fluorescence intensity from Live/Dead staining with live and dead controls shown.

Figure 35:
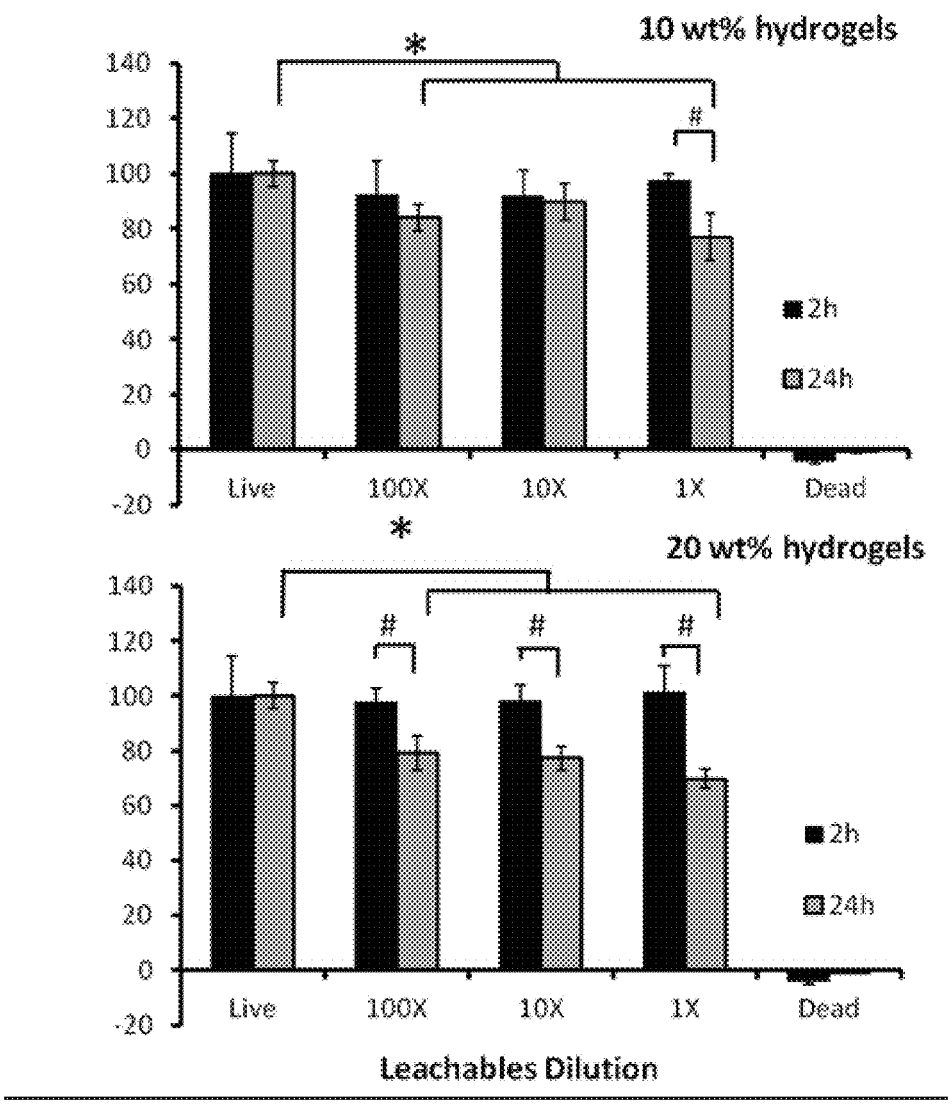

FIG. 35 shows in vitro leachables cytocompatibility of dual gelling hydrogels for two TGM wt %. Cell viability for all groups was greater than 65%. * and # indicate statistical significance (p<0.05) within and between timepoints, respectively.

Figure 36A:
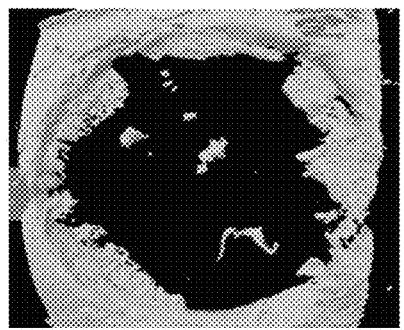
Figure 36B:
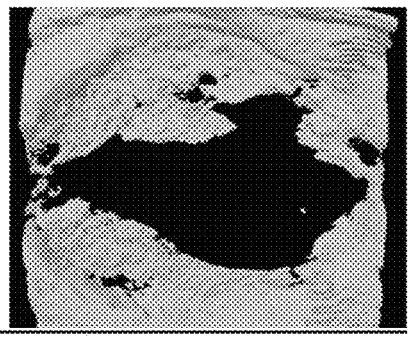

FIGS. 36A and 36B show MicroCT images of 20 wt % hydrogels in the 8 mm rat calvarial defect at 4 (FIG. 36A) and 12 (FIG. 36B) weeks.

Figure 37:
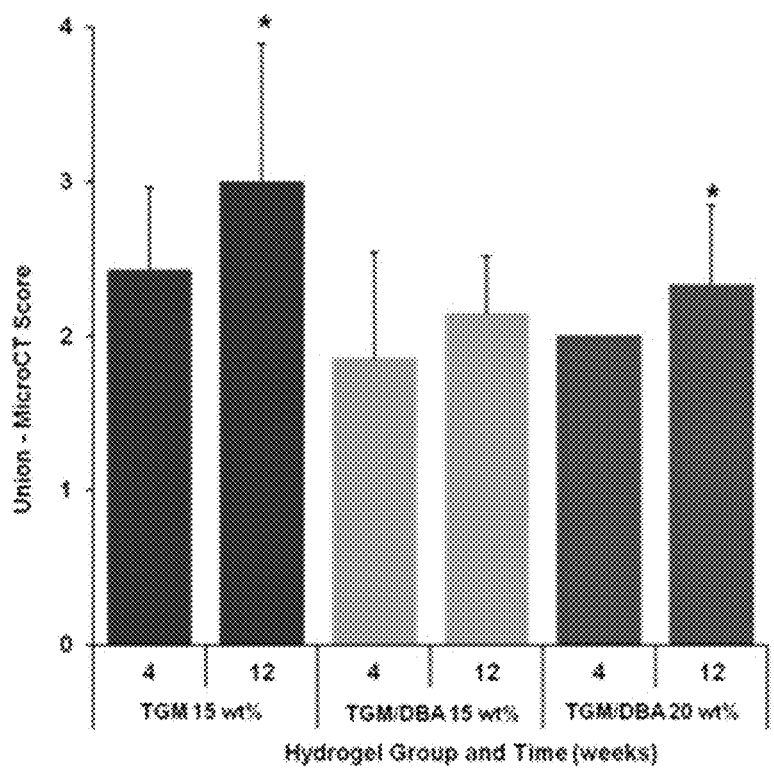

FIG. 37 shows the results of microCT scoring for bony bridging and union for 15 wt % TGM hydrogels and 15 and 20 wt % TGM/DBA hydrogels at 4 and 12 weeks. Error bars represent standard deviations for n=6-7. (*) indicates significant change from 4 week timepoint (p<0.05).

FIG. 38 shows the results of microCT quantification of % bone volume within the cranial defect at 4 and 12 weeks using an 8 mm VOI with thresholding gray values (70-255). Error bars represent standard deviation of n=6-7 hydrogels. (*) and (#) indicate significant change between timepoints or across groups, respectively (p<0.05).

FIGS. 39A, 39B, 39C, 39D, 39E, 39F, 39G, 39H, 39I, 39J, 39K, 39L, 39M, 39N, and 39O show representative top (FIGS. A-E) and side (FIGS. F-J) views of microCT generated three dimensional models showing mineralization on a binary threshold (70-255) and raw coronal cross-sections from the center of the defects (FIGS. K-O) of 15 wt % TGM at 4 (FIGS. A,F,K) and 12 weeks (FIGS. B,C,G,H,L,M) and 20 wt % TGM hydrogels at 12 weeks (FIGS. D,E,I,J,N,O).

FIGS. 40A, 40B, 40C, 40D, 40E, and 40F show histological staining of 15 wt % TGM/DBA (left column), 20 wt % TGM/DBA (middle column), and 15 wt % TGM hydrogels (right column) at 4 (FIGS. A-C) and 12 (FIGS. D-F) weeks. One set of respective images from each timepoint show von Kossa, hematoxylin and eosin, and Goldner's Trichrome staining (top to bottom) at 2× magnification. Subsets at bottom demonstrate tissue response at 12 weeks at 20× magnification within the boxed regions. Scale bars for hydrogel slices represent 1 mm and 8 mm, respectively. Scale bars for high magnification images represent 100 μm.

Figure 41:
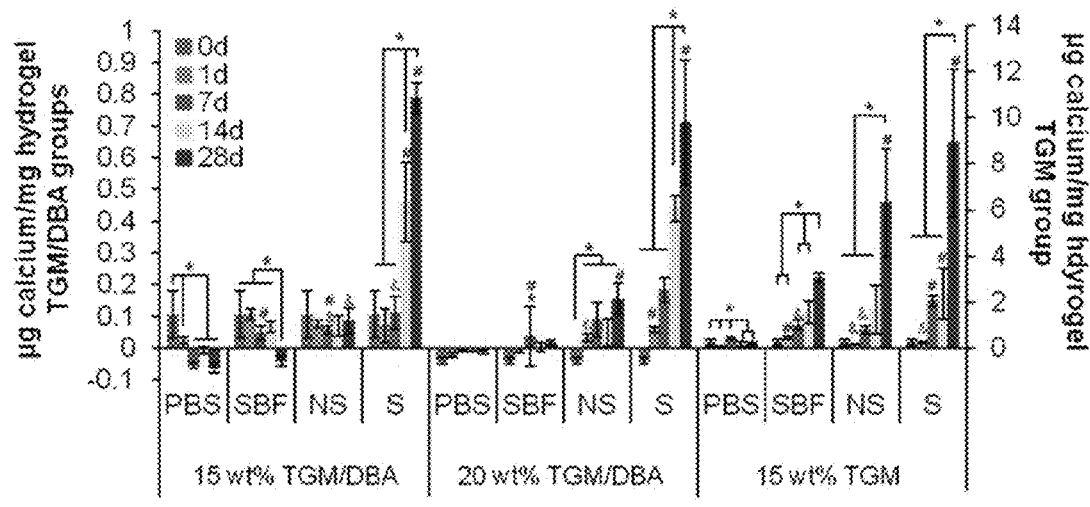

FIG. 41 shows a bar graph quantifying the calcium content of 15 wt % TGM and 15 and 20 wt % TGM/DBA acellular hydrogels (n=4) over 28 days in phosphate buffered saline (PBS), 1× simulated body fluid (SBF), complete osteogenic media without serum (NS), and complete osteogenic media with serum (S). 15 and 20 wt % TGM/DBA hydrogels correspond to the left y-axis, and 15 wt % TGM hydrogels correspond to the right y-axis. (*) refers to significant difference across timepoints within group and media (p<0.05) and (#), (&) refers to significant difference of media within group and timepoint from PBS group, and bars without similar symbols are significantly different (p<0.05).

Figure 42A:
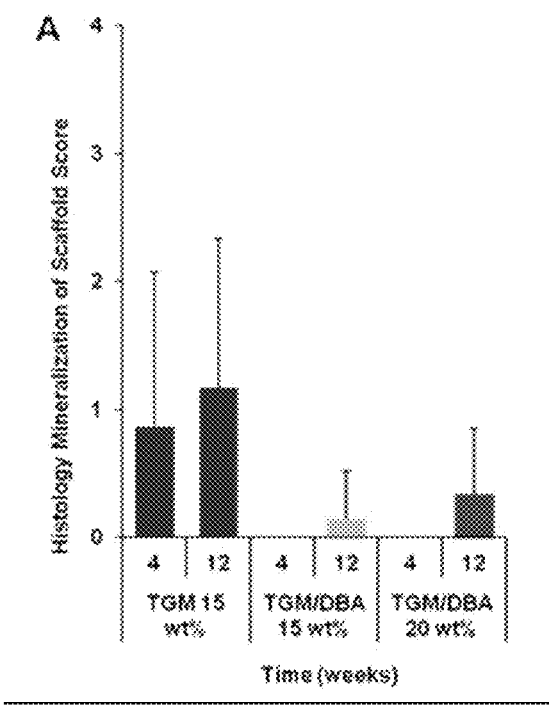

FIG. 42A shows the results of histological scoring of scaffold mineralization across the coronal cross-section in the center of the defect at 4 and 12 weeks for 15 wt % TGM hydrogels and 15 and 20 wt % TGM/DBA hydrogels. Error bars represent the standard deviation for n=6-7 samples. (*) and (#) indicates significant change across groups at same timepoint or from 4 week timepoint, respectively (p<0.05).

Figure 42B:
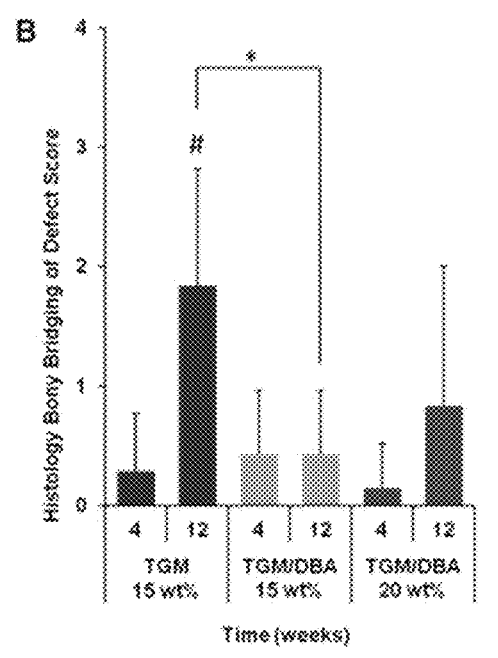

FIG. 42B shows the results of histological scoring of bony bridging across the coronal cross-section in the center of the defect at 4 and 12 weeks for 15 wt % TGM hydrogels and 15 and 20 wt % TGM/DBA hydrogels. Error bars represent the standard deviation for n=6-7 samples. (*) and (#) indicates significant change across groups at same timepoint or from 4 week timepoint, respectively (p<0.05).

Figure 43:
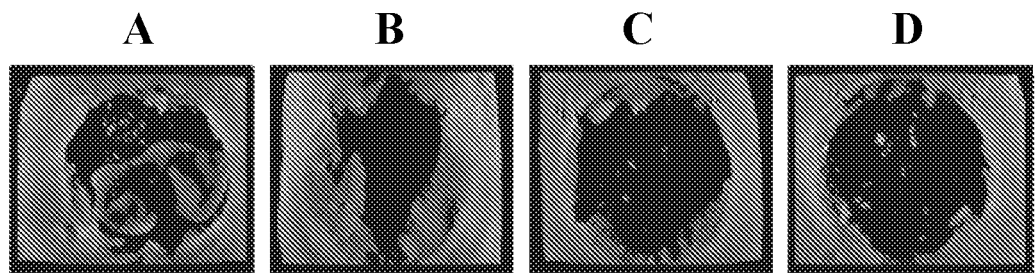

FIG. 43 depicts microCT maximum intensity projections of (A) 15 wt % TGM 12 wk, (B) 20 wt % TGM/DBA 12 wk, (C) 20 wt % TGM/DBA 4 wk, and (D) 15 wt % TGM/DBA 4 wk.

While the present disclosure is susceptible to various modifications and alternative forms, specific example embodiments have been shown in the figures and are herein described in more detail. It should be understood, however, that the description of specific example embodiments is not intended to limit the invention to the particular forms disclosed, but on the contrary, this disclosure is to cover all modifications and equivalents as illustrated, in part, by the appended claims.

DESCRIPTION

The present disclosure generally relates to injectable compositions. More particularly, the present disclosure relates to injectable, thermogelling hydrogels and associated methods.

Injectable hydrogel scaffolds can be minimally invasive and can easily fill complex tissue defects or voids often found in applications such as craniofacial bone regeneration after trauma, tumor resection, or birth defects. Thermogelling polymers, such as poly(N-isopropylacrylamide), which pass through a lower critical solution temperature (LCST) upon injection into the body, are promising candidates as scaffold backbones. Concomitant chemical crosslinking during thermogellation may further enhance the stability and mechanical properties of such materials; however these networks may need to be made biodegradable on an appropriate timescale for tissue regeneration. This may be a major issue for injectable materials, since many commonly used biodegradable polymers, such as poly(a-hydroxy esters), may not be water soluble.

While the majority of effort in tissue engineering research has been focused on pre-formed implantable scaffolds, there are many applications that might be better served with injectable, in situ forming materials capable of co-delivering cells and growth factors to optimize tissue regeneration. Injectable hydrogel-forming solutions can be applied via minimally invasive approaches, have generally high water contents to promote diffusion of nutrients and cells, and can easily fill complex tissue defects or voids often found in applications such as craniofacial bone regeneration after trauma, tumor resection, or birth defects. Various materials approaches to designing injectable hydrogel constructs have been previously reviewed.

Thermogelling polymers, which pass through a lower critical solution temperature (LCST) upon injection into the body, are promising candidates as scaffold backbones. In particular, hydrogels based on poly(N-isopropylacrylamide) (pNiPAAm), have been shown to have versatile and facile application towards the design of in situ forming hydrogel formulations. Previous efforts have identified numerous means to alter and control the rate and nature of the thermally-induced coil-globule phase transition of pNiPAAm to allow for system optimization, have demonstrated the ability to successfully deliver encapsulated cells in vitro, and have tested for efficacy as injectable biomaterials in vivo. However, one major challenge associated with using thermoresponsive materials for the design of injectable constructs concerns the tendency of such polymeric gels to undergo syneresis after initial formation. In order to explore efficient therapies that ensure complete filling of tissue defects and promote contact and the exchange of nutrients and cells with the surrounding native tissue, this limitation must be addressed.

Recent investigations have focused on the creation of dual-hardening injectable hydrogels, which combine thermoresponsive polymers with concomitant in situ crosslinking to stabilize and strengthen the constructs. While some have utilized click chemistries to this end, many investigations have created crosslinking capacity in pNiPAAm hydrogels through polymer pendant-group modification to introduce reactive double bonds. However, such systems require generally cytotoxic initiators and/or catalysts to be included in the injectable formulation to achieve crosslinking. Macromers of pNiPAAm modified with acrylate and methacrylate groups have been shown to be cytotoxic as well, thus necessitating a rapid completion of the crosslinking reaction, which is generally accomplished through inclusion of catalyst compounds and/or high initiator concentrations. Despite these cytotoxicity concerns, pNiPAAm-based dual-hardening hydrogels have had some success at maintaining the viability of encapsulated mesenchymal stem cells and promoting construct mineralization. An additional concern here is the ability of such crosslinks to degrade on a physiologically relevant timescale, as ester bonds located proximal to a polymer backbone are quite slow to degrade. Thus, additional measures must be taken to promote network degradation, such as synthesis of complex pendant groups or introduction of degradability into the pNiPAAm backbone.

In contrast to the use of a single macromer to both physically and chemically gel in situ, two-macromer systems offer a number of advantages. Key hydrogel properties, including hydrophilicity/degree of syneresis and the extent of crosslinking can be altered at the hydrogel formulation stage, as opposed to the macromer synthesis stage, through combination of a thermogelling macromer and a hydrophilic crosslinking macromer. By utilizing cytocompatible and degradable crosslinkers, optimization of the degradation and thermoresponsive behavior of the hydrogels can be compartmentalized. This route of construct design also allows for simplified and cost-effective polymer synthesis and access to a wide range of crosslinking chemistries. However, material choice is limited to water-soluble, injectable polymers, which precludes use of many commonly employed degradable polymers, such as α-hydroxy esters.

Polyamidoamines (PAMAMs) are an emerging class of water-soluble and degradable macromers, thus far used primarily in the design of dendritic polymers and gene transfection agents. They have reported biocompatibility and facile synthesis procedures. The nature of the polyaddition reaction used in PAMAM synthesis, as shown in FIG. 5, allows for the straightforward production of linear, difunctional macromers with either amine or acrylamide termini. In addition, the rate of macromer degradation can be modulated through appropriate selection of the diamine and bisacrylamide comonomers, and additional reactive pendant moieties, such as hydroxyl or carboxylic acid groups, or higher-functionality crosslinkers can be easily incorporated into the macromer design.

Thus, the present disclosure provides for a novel hydrogel system. In particular, the hydrogels of the present disclosure are injectable, thermally responsive, chemically crosslinkable, and hydrolytically degradable. In certain embodiments, the hydrogel may serve as an injectable scaffold.

Without wishing to be bound by limitation, it is believed that the combined use of a physical thermogelling and chemical crosslinking system allows for enhanced mechanical properties and reduced syneresis, or the expulsion of liquid from the gel. Previous work has shown that thermogelling poly(N-isopropylacrylamide) (PNiPAAm)-based hydrogels crosslinked via methacrylate groups are cytocompatible and mineralize in vitro. However these thermosensitive PNiPAAm-based gels undergo significant syneresis and produce non-soluble degradation products.

The present disclosure provides for a novel system that is capable of addressing both issues through the inclusion of water-soluble crosslinkers and a hydrolyzable chemical moiety that impart non-shrinking and degradative properties to injectable hydrogel compositions.

Figure 1:
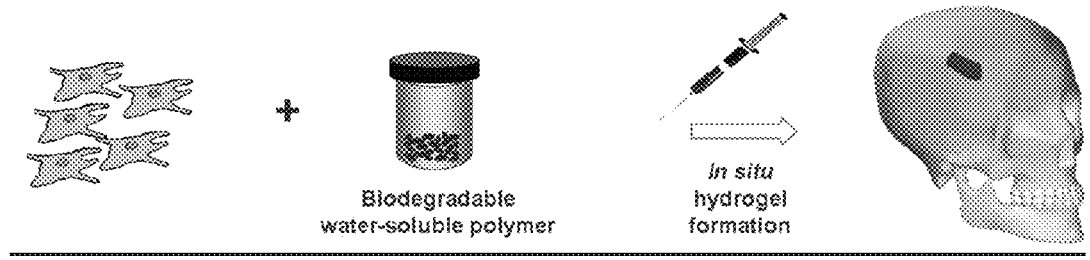
FIG. 1 is drawing that illustrates a system for injectable tissues engineering scaffolds.
Figure 2:
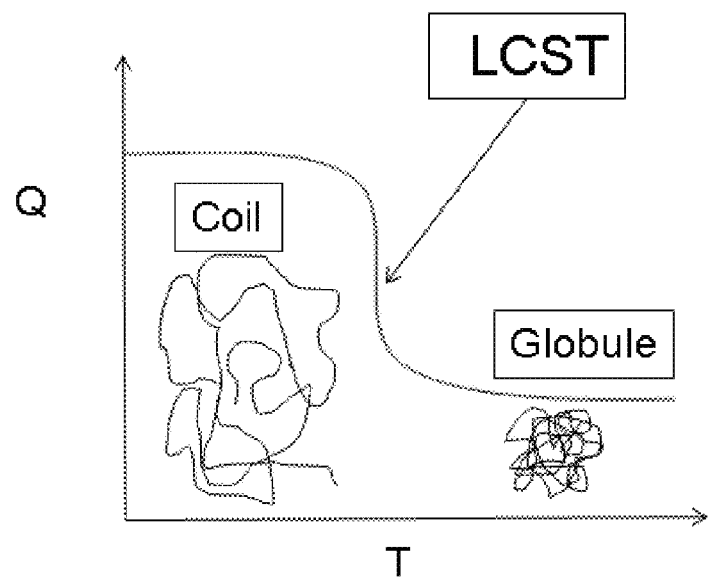
FIG. 2 is a graph that illustrates the LCST concept.

The lower critical solution temperature (LCST) is the phase transition temperature in which a mixture changes from a soluble to insoluble state. The significance of this temperature in developing injectable hydrogels of the present disclosure is that a solution may be injected into the body as a liquid and, upon passing the LCST, can instantaneously gel and form to the complex space of a defect or void. FIG. 2 illustrates this concept.

The compositions of the present disclosure generally comprise thermogelling macromers based on pNiPAAm and hydrophilic and degradable PAMAM-based macromers. The PAMAM-based macromers serve as a crosslinker in the compositions of the present disclosure. The compositions of the present disclosure may allow for dual-hardening, injectable hydrogels. One advantage of the hydrogel compositions of the present disclosure is that the rate of degradation of the hydrogels may be easily tuned through alteration of the PAMAM backbone. This is especially beneficial for tissue engineering application.

In certain embodiments, the thermogelling macromers may have the following structure:

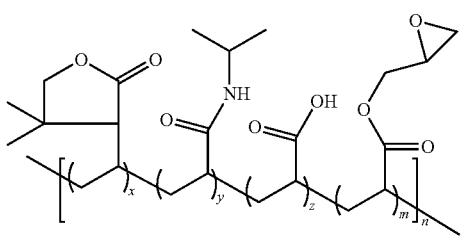

wherein x, y, z, and m are set forth as shown in FIG. 4, and wherein x is in the range of from about 0 to about 10 mol %, z is in the range of from about 0 to about 10 mol %, m is in the range of from about 2.5 mol % to about 15 mol %, and y is in the range of from about 65 mol % to about 97.5 mol %. n may be greater than or equal to 1. The molecular weight of the thermogelling macromers may vary depending on the intended application of the macromers. In certain embodiments, the number average molecular weight can vary from about 2000 to about 100,000 Da. In certain embodiments, when the composition may be used for a mammal, the number average molecular weight may be less than 32,000 Da. The order of the components of the thermogelling macromer are not limited to the order illustrated above.

In certain embodiments, the pNiPAAm-based macromers may be co-polymerized with other groups that may aid in modulating LCST. For example, the pNiPAAm-based macromers may be copolymerized and modified with pendant lactone rings. Copolymerizing the pNiPAAm-based macromers with pendant lactone rings may enable hydrolysis-dependent degradation via LCST modulation. Incorporation of the ringed monomer, for example, dimethyl-γ-butryolactone (DBA), may provide hydrolysis-dependent LCST-modulating abilities over time for the creation of soluble byproducts. FIG. 3 illustrates this basic concept. For example, DBA comonomer may modulate LCST through hydrolysis of lactone rings and DBA comonomer may decrease LCST. The presence of hydroxyl groups increases the hydrophilicity of thermogelling macromers so that the polymer may revert back to soluble macromer units. FIG. 3A illustrates hydrolysis of DBA. FIGS. 3B and 3C show the LCST modulation effect that DBA may have on a polymer with varying DBA content. Other LCST modulating groups that may be copolymerized with pNiPAAm-based macromers include but are not limited to acrylic acid (AA), glycidyl methacrylate (GMA), acrylamide (AAm) and hydroxyethyl acrylate (HEA). For example, AA and AAm comonomers may increase LCST while GMA may decrease LCST. The degree to which the LCST modulation is desired will intend on the intended application of the composition of the present disclosure.

In one embodiment, thermogelling macromers may be p(NiPAAm-co-GMA). In other embodiments, the thermogelling macromers may be p(NiPAAm-co-GMA-co-DBA-co-AA). In other embodiments, the thermogelling macromers may be p(NiPAAm-co-AAm-co-HEA)). In other embodiments, the thermogelling macromers may be p(NiPAAm-co-GMA-co-AAm).

In one embodiment, the PAMAM-based macromers may be an epoxy-reactive polyamidoamine diamine crosslinkers. Diamine functionalized polyamidoamine crosslinkers may increase the equilibrium degree of swelling through epoxy-based reactions with glycidyl methacrylate moieties of the base polymer to create non-shrinking injectable hydrogels. In another embodiment, the PAMAM-based macromers may be functionalized with bisacrylamide. PAMAM-based macromers used in conjunction with the compositions of the present disclosure have certain advantages. They are easily synthesized, allowing for flexibility. In certain embodiments, they may be the polycondensation product of bisacrylamide and diamine monomers. They are biodegradable through amide bonds, water soluble, and have reported biocompatibility.

The compositions of the present disclosure may also be used to deliver cells or other biochemical agents. In certain embodiments, PNiPAAm-based macromers may be combined with cells. In certain embodiments, the cells may be multipotent mesenchymal stem cells. The mesenchymal stem cells may be subsequently encapsulated and evenly dispersed within the polymer network upon thermogelation above the LCST. In certain embodiments, the hydrogel compositions of the present disclosure may provide a means by which localized and minimally invasive cell delivery may be achieved within a mammal. In certain other embodiments, the hydrogel compositions of the present disclosure may be used to deliver growth factors or a combination of growth factors and cells to a specific location within a mammal.

The compositions of the present disclosure may provide certain advantages. Network formation through the epoxy crosslinking reaction may be rapid and facile. In certain embodiments, the reaction may reach completion in less than three hours after an initial thermogellation time of 2-3 seconds. Additionally, the often problematic tendency of thermogelling systems to undergo significant post-formation gel syneresis may be mitigated through the combination of increased hydrogel hydrophilicity and gel hardening through concomitant chemical crosslinking during and after initial thermogellation.

Such in situ dual-hardening, dimensionally stable, defect-filling, and degradable hydrogels with high gel water content are attractive substrates for tissue engineering and cellular delivery applications. In particular, the use of water-soluble and degradable polyamidoamine macromers offers tremendous synthetic flexibility and control over subsequent gel properties. The hydrogel compositions of the present disclosure also allow for the ability to tune hydrogel hydrophilicity, degree of post-formation swelling or syneresis, degradation timescale, degree of crosslinking, and potential introduction of additional pendant functional moieties with appropriate selection of starting comonomers.

The compositions of the present disclosure solidify or gel thorough a dual-gelation, physical and chemical mechanism upon preparation and elevation of temperature. In certain embodiments, the temperature may be approximately 37° C. In certain embodiments, the compositions may solidify in situ. In certain embodiments, the increased hydrogel hydrophilicity due to increasing PAMAM-based macromer incorporation into the polymer network mitigates the often problematic tendency of thermogelling materials to undergo significant syneresis after hydrogel formation. In certain embodiments, an epoxy-based crosslinking reaction allows for rapid and facile incorporation of the PAMAM-based macromers into the polymer network during and after thermogellation. In certain embodiments, when thermogelling macromers contains GMA, the compositions may solidify and form via epoxy reactive crosslinking between GMA moieties on the thermogelling macromer and PAMAM units. (FIG. 6).

In certain embodiments, the thermogelling macromers based on pNiPAAm may be synthesized by free radical polymerization. In certain embodiments, the PAMAM-based macromers may be synthesized by polymerization of methylene bisacrylamide and piperazine.

To form the hydrogel compositions of the present disclosure, pNiPAAm-based macromers and PAMAM-based macromers are combined. The pNiPAAm-based macromers and PAMAM-based macromers may be combined in any ratio depending on the intended application and desired properties of the hydrogel. In certain embodiments, the pNiPAAm-based macromers may be present in the hydrogel composition in a range of from about 5 wt % to about 25 wt %. In certain embodiments, the pNiPAAm-based macromers may be present in the hydrogel composition in the range of from about 10 wt % to about 20 wt %. In certain embodiments, pNiPAAm-based macromers may be present in the hydrogel composition in the range of from about 15% to about 20%.

The PAMAM-based macromers may be present in the hydrogel composition of the present disclosure in an amount dependent on the amount of epoxy ring functional groups on the pNiPAAm-based macromer backbone. In certain embodiments, the PAMAM-based macromers may be present in the hydrogel composition based on the functionality ratio (molar ratio of PAMAM amine functional groups to epoxy ring functional groups.) In certain embodiments, the the PAMAM-based macromers may be present in the hydrogel composition in an amount in the range of from about 1.3 wt % to about 31.2 wt % of the hydrogel composition. However, the amount of PAMAM-based macromers and pNiPAAm-based macromers may be varied depending on the intended application of the hydrogel compositions.

The resulting macromer solution may then be exposed to an elevated temperature to allow for the solution to solidify due to thermogellation. In certain embodiments, the temperature may be about 37° C. The solidified hydrogels are stabilized and further hardened through epoxy-based chemical crosslinking, which creates a degradable polymer network structure.

In one embodiment, the present disclosure provides an injectable, thermogelling tissue engineering scaffold that comprises polyamidoamine. In another embodiment, the present disclosure provides an injectable PNiPAAm-based scaffold with tunable LCST.

The hydrogel compositions of the present disclosure may be used as an injectable scaffold to treat a defect within a mammal. In certain embodiments, the defect may be a craniofacial defect. Injectable, in situ forming materials capable of delivering both cells and growth factors are viable alternative treatments for the regeneration of bone tissue in complex craniofacial defects. Tissue engineering strategies involving injectable, in situ forming hydrogel scaffolds capable of mesenchymal stem cell (MSC) delivery show promise for regenerating complex craniofacial defects. Hydrogels based on Poly(N-isopropylacrylamide) (PNiPAAm) are particularly attractive since MSCs can be easily mixed with the polymer solution at room temperature, and subsequently be encapsulated and evenly dispersed within the insoluble network upon thermogelation above the lower critical solution temperature (LCST).

Delivery of multipotent mesenchymal stem cells (MSCs) within in situ hardening hydrogel networks may be a viable alternative for bone regeneration in defects of any shape. It has been has shown that MSC encapsulation in a thermally and chemically crosslinked poly(N-isopropylacrylamide) (PNiPAAm)-based hydrogel consisting of PNiPAAm, pentaerythritol diacrylate monostearate (PEDAS), acrylamide (AAm) and 2-hydroxyethyl acrylate (HEA) may induce osteogenic differentiation and mineralization in vitro. Klouda et al. demonstrated these hydrogels enabled osteogenic differentiation of encapsulated MSCs in vitro.

The hydrogel compositions of the present disclosure are generally biodegradable and produce non-toxic degradation products that are soluble. The rate of degradation of the solidified hydrogel likewise should not impede neotissue formation when the hydrogel composition is used as a scaffold in a mammal. Moreover, the hydrogel compositions of the present disclosure should be biocompatible.

To facilitate a better understanding of the present disclosure, the following examples of certain aspects of some embodiments are given. In no way should the following examples be read to limit, or define, the entire scope of the disclosure.

EXAMPLES

Example 1

Injectable, PNiPAAm-Based Scaffolds with Tunable LCST for Craniofacial Bone Regeneration Some objectives of this example were to synthesize a thermogelling PNiPAAm-based polymer incorporating DBA, acrylic acid (AA) and glycidyl methacrylate (GMA) monomer units, combine it with a polyamidoamine (PAMAM), epoxy-reactive crosslinker to reduce syneresis, and investigate the swelling, degradation and compressive mechanical properties of these injectable scaffolds.

Materials and Methods:

Thermogelling macromers (TGMs) were prepared with PNiPAAm, GMA, AA and DBA, via free radical polymerization. Different compositions of PAMAM crosslinker were created using a simple polymerization following established protocols. Characterization of the TGMs and percent incorporation of AA were found using proton nuclear magnetic resonance spectroscopy ($^1$H NMR) and titration, respectively. The effect of pH and percent DBA incorporation on the initial LCST was measured in a one month degradation study at 37° C. using differential scanning calorimetry (DSC) and 1H NMR. A factorial design study was performed to determine the effects of high and low TGM weight percent, DBA incorporation, PAMAM crosslinker length and crosslinker density on gelation and equilibrium swelling (FIG. 7). Several conditions were selected for further mechanical testing utilizing a thermomechanical analyzer and degradation studies.

Results and Discussion:

Gels using thermoresponsive, chemically crosslinked macromers are illustrated in FIG. 8. TGMs with GMA crosslinked with PAMAM thermogelled and crosslinked rapidly without syneresis at 37° C. Swelling studies demonstrated that gels with higher crosslinking densities and lengths exhibited greater swelling than other groups. (FIG. 7). Degradation studies without the crosslinker showed that at neutral and basic pH, hydrolysis of the DBA lactone ring was enhanced, raising the initial peak LCST from 26.0+0.6° C. to about 31° C. in 28 days (as shown in FIG. 9), which was mirrored in further gelation studies. The loss of thermogelling activity (indicated by the color change in FIGS. 8b and 8c) was caused by an increase in the LCST above 37° C. due to the basic PAMAM crosslinker, which rapidly catalyzed the degradation of DBA, leaving a fully crosslinked, but no longer thermogelled, hydrogel after 30 minutes.

Conclusions:

The presence of dual thermal and chemical hardening mechanisms allowed for instantaneous scaffold formation upon injection and reduced subsequent hydrogel syneresis, which is beneficial for the 3D incorporation and proliferation of cells. A promising system was developed for injectable craniofacial tissue regenerating therapies. It was also determined that dimethyl-y-butryolactone successfully modulates LCST, PAMAM-GMA epoxy crosslinking with PNiPAAm can create thermogelling and chemically crosslinking gels, and hydrogel properties can be tuned with different parameters.

Example 2

Injectable, Thermogelling Tissue Engineering Scaffolds Utilizing Polyamidoamines Materials and Methods:

PNiPAAm was copolymerized firstly with 2-hydroxyethyl acrylate (HEA) and acrylamide and secondly with glycidyl methacrylate (GMA) following previously established synthesis and purification protocols. Polymer composition was determined by $^1$H NMR; molecular weight by GPC; LCST by differential scanning calorimetry (DSC) and rheology. Polyamidoamine crosslinkers were created from piperazine and methylene bisacrylamide following previous synthesis procedures with both diamine (PAMAM) and diacrylamide (P-BA) products. Molecular weight and product distribution was determined by MicroTOF mass spectrometry. Polymers incorporating HEA were chemically modified with methacryloyl chloride according to established protocols to introduce reactive double bonds, combined with P-BA crosslinkers, and scaffold formation was performed as previously reported. Polymers containing GMA were combined with PAMAM crosslinkers and injected into moulds with varying setting times after mixing. Factorial designs were performed on both systems to evaluate the effects of PAMAM molecular weight, PAMAM/crosslinking density, and wt % of thermogelling polymer used for injection. Select systems were further evaluated with mechanical testing and degradation studies.

Results and Discussion:

A significant concern often encountered in systems seeking to utilize a polymer's LCST for in situ scaffold formation is the subsequent syneresis of the gel after initial formation. A previously developed system was optimized to reduce and eliminate observed scaffold syneresis and enhance network degradation on an appropriate timescale through the introduction of P-BA as a crosslinking molecule to form gels such as the one seen in FIG. 10.

Separately, a system was designed to leverage the benefits of polyamidoamines to avoid the use of free radical crosslinking pathways in favor of an epoxy-based crosslinking mechanism. PAMAM crosslinkers were combined with p(NiPAAm-co-GMA) to produce thermogelling and rapidly crosslinking gels. The extent of syneresis or swelling after initial formation was tunable through appropriate selection of system variables. FIG. 11 shows weight swelling ratios at formation and equilibrium for 10 and 20 wt % thermogelling polymer solutions in PBS (pH=7.4) with a 1.8 kDa PAMAM crosslinker with three values of crosslinker incorporation. FIG. 12 shows accelerated (pH=10) degradation profiles of two formulations with varying PAMAM molecular weight (1.8 and 2.6 kDa).

Conclusions:

Polyamidoamines were shown to be a versatile and promising material for tissue engineering, particularly in injectable applications. The systems designed were highly tunable, from the degree of syneresis or swelling of scaffolds post-formation to the timescale of degradation of the polymer network.

Example 3

The objectives of this example were: (1) develop novel, injectable, dual-hardening hydrogel scaffolds for craniofacial tissue regeneration, (2) synthesize and characterize P(N-isopropylacrylamide)-based thermogelling macromers and polyamidoamines, (3) determine efficacy and kinetics of in situ hydrogel formation, and (4) investigate effects of macromer properties and formulation parameters on hydrogel swelling, degradation, and moduli. General approaches taken include studying (1) injectable, in situ hardening materials, (2) the thermogellation mechanism, (3) in situ crosslinking (the desire to avoid syneresis and complete crosslinking over 2 hours or less), and (4) biodegradability (non-toxic degradation products, soluble degradation products, and appropriate degradation rates).

FIG. 13 illustrates a polyamidoamine. The polyamidoamine may be a polycondensation product of bisacrylamide and diamine monomers. The benefits of using these compounds are: (1) the macromers are water soluble, (2) they are biodegradable through amide bonds, (3) they are reported to be compatible, and (4) they have synthetic flexibility to tune degradation rate.

FIG. 14A illustrates one synthesis scheme for a thermogelling macromer (TGM). FIG. 14B also shows $^1$H NMR spectrum for the TGM. TGM characterization results indicated that the TGM had 7.44 mol % GMA. $M_n$ was equal to 8.86 kDa as determined by GPC. Finally, the LCSTs of the TGM were determined by DSC. The onset and peak LCST at 10 wt % in PBS pH 7.4 were 22.2±0.7° C. and 30.9±0.4° C., respectively.

FIG. 15 illustrates the synthesis of a polyamidoamine (PAMAM) and its characterization.

FIG. 16 illustrates a TGM/PAMAM gelation factorial study. In general, PAMAM and p(NiPAAm-co-GMA) were mixed at 4° C. The mixture was then injected in molds at 37° C. After 24 hours, the $w_f$ (formation) was measured and the mixture was transferred to PBS pH=7.4. After 48 hours, $w_{eq}$ (equilibrium) and lyophilized $w_d$ (dry) were measured. DSC shows crosslinking reaction was completed before two hours (10 wt % TGM and 1:1 Func. Ratio).

FIG. 17 illustrates gelation and equilibrium swelling. The results indicate the production of non-shrinkable hydrogels. The results also demonstrated tunable post-gelation hydrogel expansion. Lower gelation swelling at 20 wt % occurred due to more polymer per volume. Equilibrium swelling was consistent for 10 wt % and 20 wt % gels.

FIG. 18 illustrates factorial study results. The results indicated that longer PAMAMs increased swelling, longer preparation time increased swelling, and the degree of crosslinking had little effect, while the hydrophilicity of the hydrogel dominated. Higher polymer content improved compressive strength, while Young's Modulus decreased by approximately 50$ for 0.5:1 func. ratio.

FIGS. 19 and 20 illustrates PAMAM degradation results. Higher molecular weight PAMAM exhibited slower rate of mass loss. This indicated that it is likely that hydrophilicity of hydrogel controls early syneresis. Increased polymer content slowed rate of gel syneresis/mass loss. Hydrogel degradation at pH 7.4, 37° C. was completed for all samples studied by 12 weeks. There was a moderate (10-25%) mass loss until 9+ week.

FIG. 21 illustrates a PAMA-BA system. FIG. 22 illustrates the results of degree of modification. FIG. 23 illustrates one example of a PAMAM-BA.

The conclusions of this example were: (1) two promising, novel hydrogel systems for biomaterials application, particularly injectable scaffolds, were synthesized, (2) hydrogels were shown to avoid often problematic issues of syneresis, (3) hydrogels were shown to degrade in an appropriate timescale for tissue regeneration applications (within 12 weeks), and (4) hydrogel formulation conditions were investigated and gel syneresis, mechanical properties and degradation timescales were highly tunable, though intertwined.

Example 4

Thermogelling Macromer (TGM) Synthesis

N-isopropylacrylamide (NiPAAm), glycidyl methacrylate (GMA), 2,2'-azobis(2-methypropionitrile) (azobisisobutyronitrile, AIBN), N,N'-methylenebisacrylamide (MBA), piperazine (PiP), and 0.1N sodium hydroxide solution were purchased from Sigma-Aldrich (Sigma, St. Louis, Mo.) and used as received. The solvents; tetrahydrofuran (THF), dimethylformamide (DMF), diethyl ether, and acetone in analytical grade, and water, acetonitrile, chloroform, and methanol in HPLC-grade; were obtained from VWR (Radnor, Pa.) and used as received. Phosphate-buffered saline (PBS) solution was mixed from powder (pH 7.4, Gibco Life, Grand Island, N.Y.), and ultrapure water was obtained from a Millipore Super-Q water system (Millipore, Billerica, Mass.).

The thermogelling macromer p(NiPAAm-co-GMA) was synthesized by free radical polymerization as shown below. Ten grams of the comonomers, NiPAAm and GMA at 92.5 and 7.5 mol %, respectively, were dissolved in 100 mL of DMF and polymerized at 65° C. under nitrogen atmosphere. AIBN was added as a free radical initiator at 0.7 mol % of the total monomer content, and the reaction mixture was continuously stirred for 20 h. The product was concentrated by rotary evaporation, dissolved in THF, and twice precipitated in at least 10-times excess of cold diethyl ether to effectively remove the unreacted monomers and low molecular weight oligomers. The final filtrate was dried under vacuum at ambient temperature to yield a fine white powder. In addition, a similar procedure was followed to create a pNiPAAm homopolymer.

Scheme 1. Synthesis of p(NiPAAm-co-GMA).

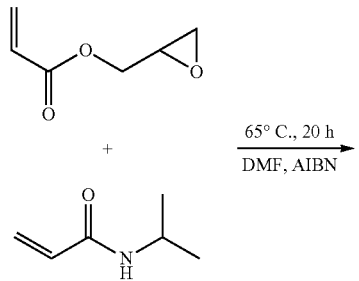

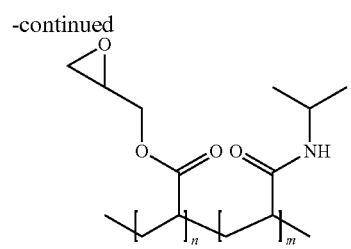

Homopolymers of pNiPAAm and copolymers with GMA were successfully synthesized to yield thermoresponsive macromers with functional pendant epoxide moieties. The number average molecular weight, $M_n$, and polydispersity index (PDI) of the synthesized pNiPAAm macromer were 8.9±0.1 kDa and 2.72±0.08, respectively, as determined by GPC (data not shown). Similarly, values of $M_n$=9.2±0.6 kDa and PDI=3.12±0.04 were found for p(NiPAAm-co-GMA).

Copolymer composition was further evaluated by $^1$H NMR. FIG. 24 shows the $^1$H NMR spectra of p(NiPAAm-co-GMA). The five individual pendant proton signals (3d and 2e) on GMA were found between 2.5 and 4.8 ppm, along with the isopropyl proton from NiPAAm (1a, 3.8-3.9). The six NiPAAm methyl protons (6b) were found from 0.9-1.3, and the polymer backbone protons (3c, 3f) were located from 1.3-2.3 ppm. The proton locations were confirmed by comparison with spectra of the NiPAAm and GMA monomers and the pNiPAAm homopolymer (data not shown). The varied peak locations allowed for five independent calculations of the GMA content in the copolymer through the relative intensities of the GMA and NiPAAm protons giving an average value of 7.44±1.12 mol %, which compares well with the theoretical GMA content (7.5 mol %).

Finally, the LCSTs of the homopolymer and copolymer were determined by DSC (FIG. 25). The onset and peak LCST for pNiPAAm were 29.5±0.2° C. and 33.3±0.2° C., respectively, which compare well with the commonly reported LCST of 32° C. Copolymerization with GMA reduced the LCST to an onset of 22.2±0.7° C. and a peak of 30.9±0.4° C. In addition, p(NiPAAm-co-GMA) displayed lower overall transition energy and a broader temperature distribution compared with the homopolymer, which can be attributed to lower overall NiPAAm content and greater chain content variation in the copolymer, respectively. The onset LCSTs as determined by DSC correlated very well to macroscopic observation of the temperatures at which thermogellation occurred (data not shown).

Example 5

Polyamidoamine Synthesis

The polyamidoamine (PAMAM) crosslinking macromers were synthesized by polyaddition of PiP with MBA (as shown below). 10.83 g of the comonomers were dissolved in 30 mL ultrapure water with a stoichiometric excess of PiP (r=[MBA]/[PiP]=0.846), stirred continuously under nitrogen atmosphere at 30° C., and allowed to react for 48 h according to published procedures (Ferruti 2002 and Dey 2005). The obtained viscous mixture was directly precipitated in 100 mL acetone, filtered, and dried under vacuum at ambient temperature to yield a fine powder.

Scheme 2. Synthesis and hydrolytic degradation of a polyamidoamine diamine macromer formed by polyaddition of piperazine and N,N'-methylenebisacrylamide.

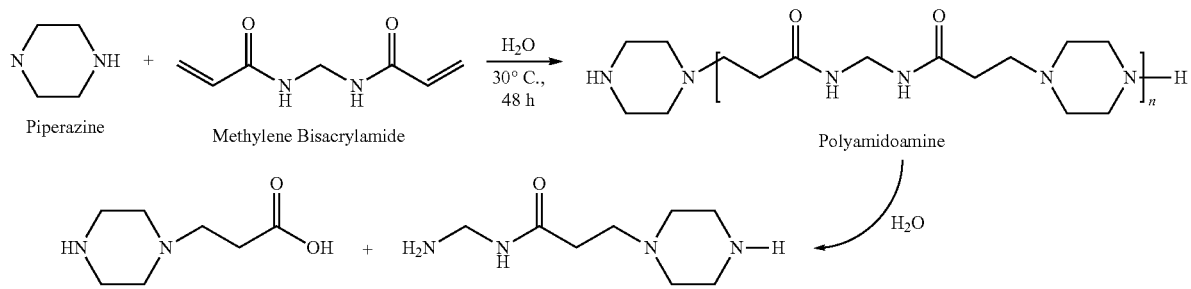

An epoxy-reactive polyamidoamine diamine crosslinker was successfully synthesized by adapting reported protocols. (Ferruti 2002 and Dey 2005). FIG. 26 shows the $^1$H NMR spectrum of the final purified and dried product of the PAMAM synthesis. The expected molecular structure of the diamine product is shown with protons and their corresponding peak locations are identified. The peak locations were confirmed by analysis of the MBA and PiP comonomers (data not shown). A crude estimate of the number average degree of polymerization can be calculated based on functional group quantification and assuming 100% conversion of the limiting reactant (MBA) as shown in FIG. 26. Application of these equations yielded r=0.840 and $X_n$=11.52 ($M_n$=1350). These values compared favorably with the feed stoichiometric ratio (r=0.846) and expected molecular weight ($X_n$=11.99, $M_n$=1400 D), assuming 100% conversion of MBA.

This molecular weight calculation assumed that all of the functional groups present were part of chains of the product diamine. However, since the product is susceptible to hydrolytic degradation and the synthesis was run in water, further analysis of the actual product compositions was necessary. To this end, time-of-flight mass spectroscopy analysis with electrospray ionization (microTOF mass spectroscopy) was utilized to identify and quantify the distribution of chain species present. FIG. 27 displays the resulting raw data of signal intensity versus absolute mass with major peaks and associated charge states identified. Charge states of peak families were determined through measurement of the separation of isomeric peaks, as shown in the insert.

MicroTOF mass spectroscopy led to the successful identification, based on expected degradation products and their subsequent potential reactions, of all major species present in the final PAMAM product, as summarized in Table 1. Each compound identified appeared at numerous molecular weights and varying charge states. In addition to proton charges, sodium and occasional potassium adducts were also observed. Thus, the peaks were deconvoluted, summed, and assigned structures with matching absolute molecular weight values: (a) is the desired diamine PAMAM product; (b) is the heteroend version of the desired product; (c) and (g) are simple degradation products; and the remainder are secondary products of the reaction of either the primary amine groups ((e) and (f)) or the carboxylic acid groups ((d) and (h)) resulting from hydrolytic degradation of the PAMAM amide linkages.

TABLE 1

Molecular structure of primary, degradation, and secondary products of the PAMAM synthesis, as determined by microTOF mass spectroscopy, and their mol % of the total species present.

| Structure | Mol % |
|---|---|
| 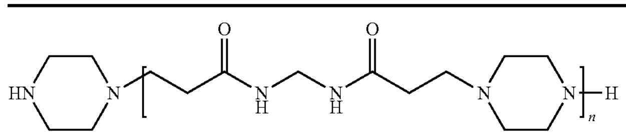 | (a) 88.5 |
| 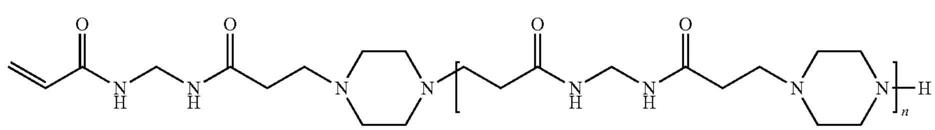 | (b) 3.7 |
| 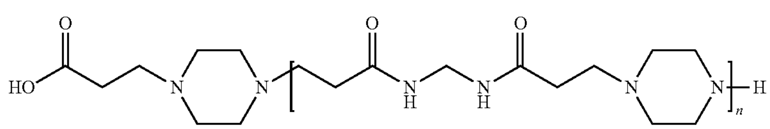 | (c) 2.7 |

TABLE 1-continued

Molecular structure of primary, degradation, and secondary products of the PAMAM synthesis, as determined by microTOF mass spectroscopy, and their mol % of the total species present.

| Structure | Mol % |
|---|---|
| 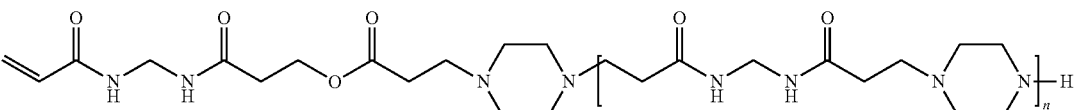 | (d) 0.5 |
| 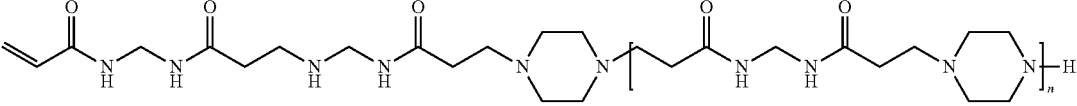 | (e) 1.3 |
| 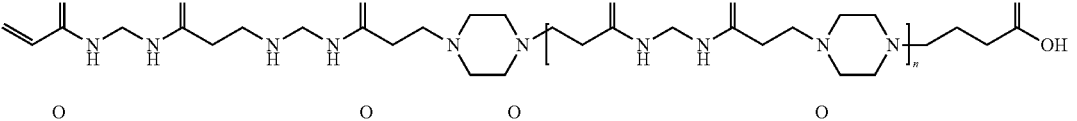 | (f) 1.4 |
| 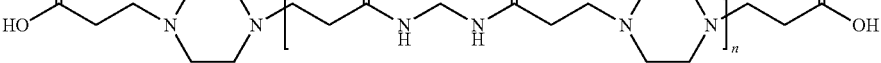 | (g) 1.6 |
| 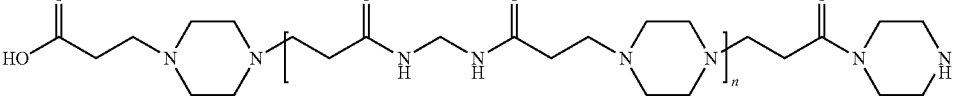 | (h) 0.2 |

It should also be mentioned that each product structure shown is the representative or simplest form of that particular product, with the degradation and secondary reaction products shown at the end of a PAMAM chain. However, further addition of repeat units is often possible beyond the end groups. Thus, each degradation and secondary reaction product shown represents a class of polymer species having the same molecular weight and functional end groups. Also shown in Table 1 are the mol percents of each species identified, as determined from the relative microTOF peak intensities, and a further product analysis is presented in Table 2.

TABLE 2

PAMAM synthesis product distribution (mol % and wt %).

| Synthesis Product | Mol % | Wt % |
|---|---|---|
| Desired Diamine | 88.5% | 95.2% |
| Heteroend Product | 3.7% | 1.3% |
| Degradation Products | 7.8% | 3.5% |
| Mono-amine | 4.7% | 2.0% |
| Other | 3.1% | 1.5% |

The desired PAMAM diamine comprises 88.5 mol % and 95.2 wt % of the total reaction product, with the difference a result of the inherently smaller nature of species originating from degradation pathways. Including the side-products and degradation-derived products of the synthesis scheme utilized, 98.5 wt % of the resultant powder will participate in epoxy reactions with the TGM macromer, with 95.2 wt % having the potential to create crosslinks and 3.3 wt % simply the potential to form hydrophilic grafts. The remaining 1.5 wt % is comprised of species with non-amine functional ends, namely carboxylic and acrylamide functional ends (structures shown in Table 1). It should be mentioned, however, that the accuracy of such compositional quantifications could be limited by the nature of the mass spectroscopy analysis. Namely, we are assuming that all species are equally ionizable, evenly electrosprayed, and the detection signal is linear over more than two orders of magnitude.

Based on initial experimental observation, it was hypothesized that the polyamidoamine reaction likely was completed much earlier than the 48 h reaction time period, which was chosen based on published reports. (Dey 2005). The hope was that optimizing the reaction timescale would result in fewer degradation and secondary reaction products. To this end, the reaction kinetics were investigated by sampling the reaction mixture over time and performing microTOF mass spectroscopy. The results of the transient reaction products study are summarized in FIG. 28, where $M_n$ and the total desired product diamine weight fraction (of the total species present in the reaction media) are shown over the course of the reaction (at 30 min, 1, 2, 4, 12, 24, and 48 h).

As hypothesized, the reaction primarily occurs and has nearly completed within the first 4 h, however no further change in the content of degradation and secondary reaction products was seen beyond the completion of the primary reaction. The absence of such a trend in retrospect can be attributed to the changing nature of the reaction media as functional groups are consumed. Namely, the rapid consumption of amine groups during the polyaddition reaction led to a significant decrease in the availability of base groups with associated decreases in the pH of the reaction solution (FIG. 28 insert). Since the hydrolytic degradation is base catalyzed, the vast majority of degradation could be anticipated to occur in the very early stages of the synthesis procedure.

This hypothesis is borne out in preliminary PAMAM and hydrogel degradation studies, where the rate of degradation is more than an order of magnitude faster at pH 10 compared to pH 7.4. The ~2 kDa $M_n$ (with a PDI of ~1.5) is higher than that found from $^1$H NMR analysis and expected from theory, but represents only the desired diamine distribution. When all species were included in the calculation, the $M_n$ was ~1.8 kDa. Finally, alternate solvents were investigated for the synthesis of the PAMAM diamine that might result in less product degradation, however due to component solubilities and the need for a protic solvent, an alternative was not identified.

Example 6

Methods for Proton Nuclear Magnetic Resonance Spectroscopy ($^1$H NMR)

$^1$H NMR spectra were obtained using a 400 MHz spectrometer (Bruker, Switzerland). Sample materials were dissolved in $D_2O$ (typical concentration: 20 mg/mL) that contained 0.75 wt % 3-(trimethylsilyl)propionic-2,2,3,3-$d_4$ acid, sodium salt (TSP) as internal shift reference (Sigma-Aldrich, St. Louis, Mo.). All post-acquisition data processing was performed with the MestRe-C NMR software package (Mestrelab Research S.L., Spain). The free induction decay (FID) was Fourier transformed, manually phased, referenced using the TSP signal, baseline corrected, and integrated.

Example 7

Gel Permeation Chromatography (GPC)

Molecular weight distributions of the p(NIPAAm-co-GMA) and pNiPAAm polymers were determined by GPC. A GPC system consisting of an HPLC pump (Waters, model 510, Milford, Mass.), an autosampler/injector (Waters, model 717), and a differential refractometer (Waters, model 410) equipped with a series of analytical columns (Styragel guard column 20 mm, 4.6×30 mm; Styragel HR3, 5 mm, 4.6×300 mm; Styragel HR1 column, 5 mm, 4.6×300 mm (all Waters)) was used with degassed chloroform as the eluent at a flow rate of 0.3 mL/min. Samples were prepared in chloroform at a concentration of 25 mg/mL and filtered prior to analysis. Macromer number average molecular weight ($M_n$) and polydispersity index (PDI) were determined in triplicate relative to polystyrene standards.

Example 8

MicroTOF Mass Spectroscopy

Molecular weight distributions of the synthesized PAMAM crosslinker were analyzed using time-of-flight mass spectroscopy with positive-mode electrospray ionization on a Bruker microTOF ESI spectrometer (Bruker Daltonics, Billerica, Mass.) equipped with a 1200 series HPLC (Agilent Technologies, Santa Clara, Calif.) to deliver the mobile phase (50:50 HPLC-grade water and methanol). During the PAMAM synthesis, 100 µL samples of the reaction mixture were collected at 30 min and 1, 2, 4, 12, 24, and 48 h, diluted with 550 µL of a 50:50 mixture of HPLC-grade water and acetonitrile with 0.1% formic acid added, and a 2 µL flow injection was delivered to the electrospray chamber. After data acquisition, all peaks (including degradation and secondary reaction products) were identified using microTOF Control software (Bruker), corrected for charge state (generally with $H^+$ or $Na^+$ and rarely $K^+$ ions), and quantified for calculation of $M_n$, $M_w$, and PDI.

Example 9

Differential Scanning calorimetry (DSC)

The LCSTs of the thermogelling macromers were determined by DSC. 14 µL of 10 wt % polymer in pH 7.4 PBS solutions were pipetted into aluminum volatile sample pans (TA Instruments, Newcastle, Del.) and capped/crimped. Thermograms were recorded in triplicate on a TA Instruments DSC 2920 equipped with a refrigerated cooling system against an empty sealed pan as reference. In a typical run, the oven was equilibrated at either 5° C. or −5° C. for 10 min and then heated to 80° C. at a heating rate of 5° C./min. The LCST was determined both as the onset and peak temperature of the endothermic peak in the thermogram using the Universal Analysis 2000 software provided with the DSC system. In addition, the progress of the hydrogel formation/crosslinking reaction was monitored by DSC. 14 µL of the hydrogel solution (10 wt % TGM and 7 wt % PAMAM in pH 7.4 PBS) was pipetted into an aluminum pan, capped/crimped, placed into the DSC and equilibrated at 37° C., and monitored until the completion of the reaction.

Example 10

Rheological Characterization

A thermostated, oscillating rheometer (Rheolyst AR1000, TA Instruments, New Castle, Del.) equipped with a 6 cm steel cone (1 degree) with a gap size of 26 µm was used to evaluate the elastic response of the hydrogels. Injectable hydrogel formulations containing 7 and 10 wt % (w/v) of PAMAM and TGM, respectively, in pH 7.4 PBS were pipetted onto the rheometer, and the dynamic viscoelastic properties of the solutions, namely, the dynamic shear storage (G') and loss (G") moduli, complex viscosity ($|\eta^*|$), and loss angle ($\delta$), were recorded using the TA Rheology Advantage software (TA Instruments) as the solution was either maintained at a temperature of 18° C. for 4 h or maintained at 4° C. for 10 minutes followed by rapid elevation to and maintenance at 37° C. for 3 h.

Example 11

Hydrogel Formation and Degradation

Individual solutions of the TGM and PAMAM macromers were prepared at twice the desired final solution concentrations, and 250 µL of each TGM and PAMAM solution combination were combined in a glass vial at 4° C. and mixed gently for ~30 s. The injectable solutions were then immediately immersed in a 37° C. water bath and allowed 24 h to reach equilibrium. After equilibrium swelling analysis, degradation of the PAMAM networks at 37° C. was evaluated in both pH 7.4 PBS and 0.1N sodium hydroxide solution.

The TGM and PAMAM macromers were combined as synthesized in pH 7.4 PBS to create injectable, in situ dual-hardening solutions. Upon macromer mixing and increasing the temperature to 37° C., the solutions will rapidly solidify due to the thermogellation mechanism. Subsequently, the hydrogels will be stabilized and further hardened through epoxy-based chemical crosslinking to create a degradable polymer network structure (FIG. 29).

FIG. 30 illustrates the effect of progressive incorporation of the PAMAM crosslinker into 10 wt % TGM injectable solutions, with the equilibrium volume swelling ratio relative to the 0 wt % PAMAM hydrogel, $Q_r$, shown. As hypothesized, the increased hydrogel hydrophilicity mitigated the often problematic tendency of thermogelling solutions to undergo significant post-formation syneresis, while maintaining the ability of the TGM to undergo thermogellation at 37° C. It should also be noted that the theoretical maximum degree of crosslinking for this particular combination of TGM and PAMAM macromers is ~7 wt % PAMAM for 10 wt % TGM, as determined from quantification of reactive amine and epoxy functionalities per unit mass for each macromer. Thus, beyond 7 wt % PAMAM, the fraction of PAMAM molecules forming intermolecular crosslinks or intramolecular loops will decrease as some are replaced by hydrophilic branches.

The kinetics of the epoxy crosslinking reaction were first monitored thermally by DSC for injectable hydrogel solutions with 10 and 7 wt % of TGM and PAMAM, respectively. As can be seen in FIG. 31, the crosslinking reaction was completed within 110 minutes. Such rapid in situ hardening of the thermogelled hydrogel constructs enhances gel stability while minimizing exposure of encapsulated cells and surrounding tissue to reactive species. Further evidence of the progress of the crosslinking reaction was seen in rheology traces. FIG. 32 shows the rheological response of the hydrogels to crosslinking both in the presence (4/37° C.) and absence (18° C.) of physical thermogellation. Thus, the dual, thermally and physically, gelling nature of the hydrogel system is clearly illustrated.

Network formation in the absence of thermogellation at 18° C. resulted in hydrogels that reached the gel point in ~100 min and had ultimate shear storage moduli, G', on the order of 1 kPa. Network formation in the presence of thermogellation at 37° C. reached the gel point at ~60 min and showed the relative contributions of the physical and thermal gelation mechanisms, with an ultimate shear storage modulus, G', on the order of 90 kPa. The timescale of the crosslinking reaction as shown by rheology was somewhat lengthier than that shown by DSC (~180 and ~110 min, respectively). This is likely a reflection of rapid initial reaction followed by slower reaction of the incorporated but unreacted (dangling) amine functionalities, with associated network rearrangement, after the onset of the chemical gelation. The even longer timescales of chemical gelation and completion of crosslinking at 18° C. was simply a reflection of lower rates of reaction and diffusion at the lower temperature.

After equilibrium swelling analysis, hydrogels were allowed to degrade at 37° C. in pH 7.4 PBS. FIG. 33 shows the rapid mass loss of the hydrogels associated with the degradation of the PAMAM crosslinkers beginning at seven and terminating at ten weeks. While this is likely to be an appropriate degradation timescale for many tissue engineering applications, it is worth pointing out once more that one of the major advantages of this novel class of polyamidoamine-based injectable hydrogels is the documented ability to easily tune the rate of polymer degradation as needed through alteration of the PAMAM backbone. Additionally, the hydrogels were evaluated under base-catalyzed accelerated degradation conditions, whereby 1 mL of 0.1N sodium hydroxide solution was added to each vial in place of PBS. Within 4 days, hydrolytic degradation of the PAMAM crosslinkers was completed in all gels to yield clear liquid solutions at 4° C. (data not shown).

Example 12

Cell Culture Studies & Cytocompatibility of Hydrogel Leachables

A rat fibroblast cell line (ATCC, CRL-1764) was cultured on T-75 flasks using Dulbecco's modified Eagle medium (DMEM; Gibco Life, Grand Island, N.Y.) supplemented with 10% (v/v) fetal bovine serum (FBS; Cambrex BioScience, Walkersville, Md.) and 1% (v/v) antibiotics containing penicillin, streptomycin and amphotericin (Gibco Life). Cells were cultured in a humidified incubator at 37° C. and 5% $CO_2$. Cells of passage number 3 were used in this study.

The cytocompatibility of the chemically and thermally gelled hydrogels were evaluated by a leachables extraction test, according to established protocols. (Klouda 2009 and Timmer 2003). Hydrogel discs were formed by injecting 90 µL aliquots of a 4° C. solution with 7 and 10 wt % PAMAM and TGM, respectively, in cell culture media (DMEM, supplemented with antibiotics) without the addition of serum into Teflon molds (6 mm in diameter and 3 mm in height) held at 37° C. and given 24 h to equilibrate. Hydrogels were then immersed in an excess of cell culture media without serum at a surface area to fluid volume ratio of 3 $cm^2$/mL and incubated at 37° C. for 24 h. (Timmer 2003). The resulting hydrogel leachables solution was collected, sterile filtered, and prepared in 1, 10, and 100× dilutions. Cultured cells were harvested at 80-90% confluency with a Trypsin/EDTA solution (2 mL/flask), resuspended at a density of 100,000 cells/mL, and seeded into 96-well tissue culture plates (100 µL cell suspension/well) for a seeding density of 10,000 cells/well. The plates were then incubated for 24-48 h before testing to achieve 80-90% confluency within the well. The three dilutions of extract media were added to the cultured fibroblast cells in the 96-well plates (100 µL/well), replacing the culture media (n=6). In addition, cells fed with identical media without the extracted leachables (DMEM supplemented with antibiotics and without serum) served as a positive (live) control, and cells exposed to 70% ethanol for 10 min served as the negative (dead) control (n=6). The plates were then incubated at 37° C., 95% relative humidity, and 5% $CO_2$ for either 2 or 24 h.

Following incubation, media were removed, the cells were rinsed three times with pH 7.4 PBS, calcein AM and ethidium homodimer-1 in 2 µM and 4 µM concentrations in PBS, respectively (Live/Dead viability/cytotoxicity kit, Molecular Probes, Eugene, Oreg.), were added, and the cells were incubated in the dark at room temperature for 30 min. Cell viability was then quantified using a fluorescence plate reader (Biotek Instrument FLx800, Winooski, Vt.) equipped with filter sets of 485/528 nm (excitation/emission) for calcein AM (live cells) and 528/620 nm (excitation/emission) for EthD-1 (dead cells). The fluorescence of the cell populations was recorded and the fractions of live and dead cells were calculated relative to the controls. The data are expressed as mean±standard deviation, and statistically significant differences were determined by Tukey's post hoc test.

Finally, initial cytocompatibility of the hydrogels was evaluated through exposure of rat fibroblasts to the soluble hydrogel leachables with fluorescent Live/Dead analysis after 2 and 24 h. FIG. 34 shows the resulting fraction of live cells treated with 1, 10 and 100× dilutions of the hydrogel leachables in media relative to the untreated live control. The hydrogels were shown to be fully cytocompatible at all conditions tested, which was largely expected from the wealth of literature showing the general cytocompatibility of PNiPAAm-based and polyamidoamine-based macromers, as discussed in the introduction.

Example 13

Biocompatibility Evaluation of Poly(N-isopropylacrylamide)-based Hydrogels for Craniofacial Bone Regeneration The objectives of this study were (i) to fabricate non-shrinking, biodegradable hydrogels by copolymerizing the PNiPAAm-based macromers with pendant lactone rings to enable hydrolysis-dependent degradation via LCST modulation and crosslinking with polyamidoamine (PAMAM) crosslinkers and (ii) to evaluate the in vitro cytocompatibility of the leachable and degradation byproducts and the in vivo biocompatibility of the injectable system in an orthotopic defect.

Thermogelling macromers (TGMs) were prepared with PNiPAAm, glycidyl methacrylate, acrylic acid and the hydrolyzable ring, dimethyl-γ-butyrolactone acrylate (DBA), via free radical polymerization by adapting the protocol as previously described (Ekenseair A K. Biomacromolecules. 2012; 13 (6):1908-1915). Low molecular weight PAMAM crosslinkers were created using a simple polymerization following established protocols (Ekenseair A K. Biomacromolecules. 2012; 13 (6):1908-1915). The cytocompatibility of TGMs and crosslinked hydrogels was assessed with a fibroblast cell line using leachable assays following previous studies (Klouda L. Biomaterials. 2009; 30:4558-4566). Cell viability was quantified using Live/Dead reagents and fluorescence plate reader and normalized to controls. In vivo evaluation of two hydrogel formulations (n=7) was performed in an 8 mm rat calvarial critical size defect following established protocols (Spicer P. Nature Protocols. 2012; 7:1918-1929). After harvest at 4 and 12 weeks, samples were analyzed with microcomputed tomography (microCT), histology and histomorphometry for biocompatibility, syneresis and mineralization.

Rapid gelling, non-shrinking hydrogels were fabricated from the mixing of TGMs with the PAMAM crosslinkers, resulting in highly swollen gels. Extensive cytocompatibility testing of the TGM and hydrogel demonstrated that hydrogel system presented little cytotoxicity, and there were no significant effects of different hydrogel parameters on cell viability except at the highest polymer densities (FIG. 35). Additionally, the hydrogels did not impede neotissue formation within the defect (FIG. 36).

The results indicate that the presence of dual thermal and chemical crosslinking mechanisms can reduce hydrogel syneresis, which is beneficial for the incorporation and proliferation of cells. Furthermore, the hydrogel leachable products demonstrate in vitro cytocompatibility and the preliminary data suggest these hydrogels are biocompatible and potentially mineralize in vivo. In combination with MSCs, this in situ forming hydrogel system may provide a novel solution for localized and minimally invasive cell delivery for craniofacial bone regeneration.

Example 14

Evaluation of Implanted Poly(N-isopropylacrylamide)-based Hydrogels in Rat Cranial Defect The objective of this study was to evaluate the mineralization capacity and biocompatibility of acellular injectable, dual-gelling hydrogels based on PNiPAAm for the healing of an 8 mm critical size rat cranial defect.

Materials and Methods:

Materials

N-isopropylacrylamide (NiPAAm), dimethyl-γ-butyrolactone acrylate (DBA), glycidyl methacrylate (GMA), acrylic acid (AA), 2,2'-azobis(2-methylpropionitrile) (azobisisobutyronitrile, AIBN), N,N'-methylenebisacrylamide (MBA), and piperazine (PiP) were purchased from Sigma Aldrich (Sigma, St. Louis, Mo.) and used as received. Anhydrous 1,4-dioxane, dimethylformamide, diethyl ether, and acetone in analytical grade; water, acetonitrile, chloroform, and methanol in HPLC-grade; and 1 N sodium hydroxide (NaOH) were purchased from VWR (Radnor, Pa.) and used as received. Phosphate buffered saline (PBS) solution was obtained from Gibco Life, Grand Island, N.Y. (powder, pH 7.4). Ultrapure water was obtained from a Millipore Super-Q water system (Millipore, Billerica, Mass.).

In Vivo Experimental Design

Three groups of acellular hydrogels were examined in an 8 mm critical size rat cranial defect, as outlined in Table 3. The first experimental group ("15 wt % TGM") consisted of the P(NiPAAm-co-GMA) TGM at 15 wt % polymer. The other two experimental groups ("15 wt % TGM/DBA") and ("20 wt % TGM/DBA") consisted of the P(NiPAAm-co-GMA-co-DBA-co-AA) TGM with the DBA-containing hydrolyzable lactone ring at 15 or 20 wt % polymer. Based on previous work with rat cranial defects, the time periods chosen were 4 and 12 weeks. At both timepoints, the samples were evaluated with microCT and histology after harvest. All groups consisted of n=6-7 rats.

TABLE 3

Study design for in vivo study

| Group | TGM composition | Thermogelling Macromer (TGM) | | Polyamidoamine (PAMAM) Crosslinker | |
|---|---|---|---|---|---|
| | | TGM wt % | Initial Peak LCST (° C.) | PAMAM $M_n$(Da) | Amine:epoxy mol ratio |
| 1 | P(NiPAAm$_{92.6}$-co-GMA$_{7.4}$) | 15 | 30.9 ± 0.4 | 1440 | 1:1 |
| 2 | P(NiPAAm$_{84.9}$-co-GMA$_{9.1}$-co-DBA$_{5.8}$-co-AA$_{3.2}$) | 15 | 22.4 ± 1.0 | 1440 | 1:1 |
| 3 | P(NiPAAm$_{84.9}$-co-GMA$_{9.1}$-co-DBA$_{5.8}$-co-AA$_{3.2}$) | 20 | 22.4 ± 1.0 | 1440 | 1:1 |

*subscripts indicate mol % of comonomer

TGM Synthesis and Characterization

Synthesis of P(NiPAAm-co-GMA) and P(NiPAAm-co-GMA-co-DBA-co-AA) TGMs were performed according to those protocols reported in Example 4 and as summarized herein below. In a typical reaction, 20 g of NiPAAm, GMA, DBA and AA was dissolved in 200 mL of either anhydrous dimethylformamide or 1,4-dioxane under nitrogen at 65° C. for the TGM and TGM/DBA groups, respectively. AIBN pre-dissolved in the solvent was added at 0.7% of total mol content to thermally initiate free radical polymerization, and the reaction mixture was stirred for 16 h. After solvent removal by rotary evaporation, the material was re-dissolved in either pure acetone or a 95:5 (v/v) mixture of acetone:methanol for the TGM/DBA and TGM groups, respectively and purified twice via dropwise precipitation in at least 10× excess diethyl ether. The recovered polymer was air-dried overnight and transferred to a vacuum oven for several days prior to elemental analysis. The chemical composition of the TGMs was determined by proton nuclear magnetic resonance spectroscopy (1H NMR, Bruker, Switzerland). The polymer was dissolved in D2O at a concentration of 20 mg/mL that contained 0.75 wt % 3-(trimethylsilyl)propionic-2,2,3,3-d4 acid, sodium salt as an internal shift reference (Sigma-Aldrich, St. Louis, Mo.) and the data were analyzed using the MestRe-C NMR software package (Mestrelab Research S.L., Spain). Acid titration was performed in conjunction with 1H NMR to determine the AA content of the TGMs before hydrolysis. Aqueous gel permeation chromatography (GPC) using a Waters Alliance HPLC system (Milford, Mass.) and differential refractometer (Waters, model 410) equipped with a series of analytical columns (Waters Styragel guard column 20 mm, 4.6×30 mm; Waters Ultrahydrogel column 1000, 7.8×300 mm) was used to determine the molecular weight distributions of the synthesized TGM/DBA polymers. The TGM/DBA polymer was first hydrolyzed in accelerated conditions to remove its thermogelling properties. The weight average molecular weight (Mw), number average molecular weight (Mn), and polydispersity index (PDI=Mw/Mn) of the hydrolyzed polymer were determined by comparison to commercially available narrowly dispersed molecular weight poly(ethylene glycol) (PEG) standards (Waters, Mississauga, ON). The LCSTs of the TGMs were determined by differential scanning calorimetry (DSC). 14 µL, of each polymer solution was pipetted into an aluminum volatile sample pan (TA Instruments, Newcastle, Del.) and capped/crimped. Thermograms were recorded on a TA Instruments DSC 2920 equipped with a refrigerated cooling system against an empty sealed pan as reference. The oven was equilibrated at −5° C. for 10 min and then heated to 80° C. at a heating rate of 5° C./min. The LCST was determined both as the onset and peak temperature of the endothermic peak in the thermogram using the Universal Analysis 2000 software provided with the DSC system. For this study, P(NiPAAm92.6-co-GMA7.4) with a Mn=~9.2 kDa and PDI of 3 and P(NiPAAm84.9-co-GMA9.1-co-DBA5.8-co-AA3.2) with a Mn=~56.1 kDa and PDI of 2 were used.

PAMAM Synthesis and Characterization

PAMAM was synthesized by the polyaddition of piperazine (PiP) and methylene bisacrylamide (MBA) at a stoichiometric ratio of [MBA]/[PiP]=0.75 as described previously herein (Example 5). Molecular weight distributions of the synthesized PAMAM crosslinkers were analyzed using time-of-flight mass spectroscopy with positive-mode electrospray ionization on a Bruker microTOF ESI spectrometer (Bruker Daltonics, Billerica, Mass.) equipped with a 1200 series HPLC (Agilent Technologies, Santa Clara, Calif.) to deliver the mobile phase (50:50 HPLC-grade water and methanol). After data acquisition, all peaks (including degradation and secondary reaction products) were identified using microTOF Control software (Bruker). The peaks were corrected for charge state (generally with $H^+$ or $Na^+$ and rarely $K^+$ ions), and quantified for calculation of $M_n$, $M_w$, and PDI. PAMAM with $M_n$=1440 Da and PDI=1.38 was used for this study.

Hydrogel Fabrication

Hydrogels (8 mm in diameter, 2 mm in height) were fabricated by combining the TGM and PAMAM crosslinker. The TGM and PAMAM crosslinker were first sterilized via UV-irradiation for 2 h. Individual solutions of TGM and PAMAM crosslinker were then prepared at twice the desired concentrations (Table 3) in sterile PBS pH 7.4 and placed on a shaker table at 4° C. until dissolved. Under sterile conditions, the PAMAM solution was pipetted into the TGM solution using cold pipet tips and the resulting solution was manually mixed in the glass vial. 110 µL injections were transferred to 8 mm diameter×2 mm height cylindrical Teflon molds at 37° C. either immediately for TGM/DBA groups or after a 20 minute delay for the TGM group, covered with a glass slide, and subsequently allowed to gel for 24 h prior to implantation.

Animal Surgeries and Euthanasia

This work was done in accordance with protocols approved by the Rice University Institutional Care and Use Committee. After hydrogel fabrication with PBS pH 7.4 under sterile conditions in 8 mm×2 mm Teflon molds, the hydrogels were implanted within an 8 mm rat cranial defect. All scaffold groups were statistically randomized to minimize operative- or animal-related error. 11-12 week Fischer 344 rats weighing 176-200 g (Harlan, Indianapolis, Ind.) were placed under 4% isoflurane and maintained at 2% isoflurane/$O_2$ gas mixture for the duration of the operation. The incision site and surrounding area were shaved, sterilized with povidine-iodine swabs, and subcutaneously injected with 500 µL of 1% lidocaine for local anesthesia. A linear incision was performed from the nasal bone to the mid-sagittal crest, and the skin and periosteum were exposed from the underlying bone. An 8 mm craniotomy was performed with a dental surgical drilling unit with a trephine burr and saline irrigation, and the calvarial disk was carefully removed to prevent dural tearing. After cleaning and removal of bone fragments, the scaffold was implanted and the periosteum and skin were each separately closed with interrupted braided Vicryl stitches. The rats were given an intraperitoneal injection of saline (1 mL/100 g/h of anesthesia) to counteract blood loss and aid recovery. Additionally, intraperitoneal injections of buprenorphine (0.05 mg/kg) were given at 12, 24, and 36 h as post-operative analgesia. After surgery, the rats were placed under pure $O_2$ until awakened from anesthesia and individually housed in soft-bedding cages. Animals were given free access to food and water and monitored for complications. The implants and surrounding tissue were harvested 4 or 12 weeks post-surgery. The rats were euthanized by $CO_2$ inhalation after anesthesia under 4-5% isoflurane, followed by a bilateral thoracotomy.

Implant Retrieval

The implants were harvested by making an incision between the medial canthi of the eyes down to the bone using a 701 burr attached to a Stryker Total Performance System straight handpiece at 40,000 rpm with water irrigation. Similar cuts were made along the left and right temporal bone and posterior aspect of the cranial vault, resulting in a rectangular section of the cranium containing the defect site and implant. The implants were fixed in 10% formalin (Formalde-Fresh, Fisher) for 3 days at 37° C. and transferred to 70% (v/v) ethanol for microCT and histological analysis.

Microcomputed Tomography

MicroCT analysis with a Skyscan 1172 High-Resolution Micro-CT (Aartselaar, Belgium) with 10 µm resolution, 0.5 mm aluminum filter, and voltage of 100 kV and current of 100 µA was used to examine the morphology and mineralization of the implants and bony union across the defect. Volumetric reconstruction and analysis was conducted using Nrecon and CT-analyser software provided by Skyscan. The percent of bone formation, including hydrogel mineralization, within the defect was determined by centering a cylindrical volume of interest (VOI) of 8 mm in diameter and 2 mm in height at the bottom of the defect. Data are reported as the % binarized object volume measured within this VOI within thresholding gray values (70-255) with the CT-analysis software as described in Henslee, A. M., et al., *Acta Biomater* 7 (10): p. 3627-37. The extent of bony bridging and union within the defect were scored according the grading scale in Table 4. These scores were determined from maximum intensity projections of the samples generated from the microCT datasets. 3D models of each sample were also generated to visualize the distribution of mineral deposits within the hydrogel implants.

Histological Processing

After microCT scanning, the samples were sent to the MD Anderson Bone Histomorphometry Core laboratory for dehydration and embedding in poly(methyl methacrylate). 5 µm coronal cross-sections were taken from the center of the defect of each sample and staining was performed with von Kossa, hematoxylin and eosin, and Goldner's trichrome.

Histological Scoring

The three histological sections were evaluated via light microscopy (Eclipse E600, Nikon, Melville, N.Y. with attached 3CCD Color Video Camera DXC-950P, Sony, Park Ridge, N.J.) and scored using histological scoring analysis. The histological evaluation was performed along random implant-tissue interfaces within central coronal cross-sections to assess: (1) overall tissue response following the rubric outlined in Table 6 in the Results below, (2) mineralization within the hydrogel following the scoring guide outlined in Table 5, and (3) extent of bony bridging across the defect following the rubric outline in Table 5. The evaluations were performed blindly with randomized samples by three reviewers. A description of the scoring system for mineralization and bony bridging is shown in Table 5.

TABLE 5

Mineralization of Scaffold and Bony Bridging Scoring Guide

| Description | Score |
|---|---|
| Mineralization of Scaffold | |
| Mineral deposition in 75-100% of the scaffold | 4 |
| Mineral deposition in 50-75% of the scaffold | 3 |
| Mineral deposition in 25-50% of the scaffold | 2 |
| Mineral deposition in up to 25% of the scaffold | 1 |
| No mineral deposition observed | 0 |
| Bony Bridging Across Full Length of Scaffold | |
| >75% bridging across defect | 4 |
| 50-75% bridging across defect | 3 |
| 25-50% bridging across defect | 2 |
| <25% bridging across defect | 1 |
| No bony bridging observed | 0 |

Acellular Mineralization

8×2 mm acellular hydrogels (n=4 per group) were fabricated as described above. The hydrogels were incubated in complete osteogenic medium without fetal bovine serum (FBS), complete osteogenic medium with 10% FBS (Cambrex Bioscience), PBS pH 7.4, and 1× simulated body fluid for 0, 1, 7, 14, and 28 days at 37° C. in 12-well plates. The simulated body fluid was prepared according to Kokubo, T. and H. Takadama, *Biomaterials,* 2006. 27 (15): p. 2907-15. Each solution was changed every 2-3 days. At timepoints, the hydrogels were soaked in ultrapure water for 30 min, cut in half, blotted and weighed. Sample halves (n=4 halves) for the calcium assay were place in 500 µL of ddH$_2$O, homogenized through three freeze/thaw/sonication cycles, and digested overnight in equal parts of 1N acetic acid for a final concentration of 0.5 N acetic acid. The assay was performed with a commercially available kit (Sekisui Diagnostics, Tokyo, Japan) according to the manufacturer's instructions. The remaining sample halves were fixed in 10% formalin, dehydrated in 70% ethanol, placed in Histoprep frozen tissue embedding media (Fischer Scientific, Waltham, Mass.), and frozen at −20° C.

Statistics

The microCT and histological scoring data were analyzed via one-way analysis of variance followed by the Kruskal-Wallis test (p<0.05) for n=6-7 samples. The microCT bone volume for n=6-7 samples and in vitro mineralization data for n=4 were presented as means±standard deviation, unless otherwise stated. The acellular mineralization data were analyzed by Tukey's post-hoc test using JMP v11 statistical software.

Results:

MicroCT analysis

Three different groups of acellular, dual-gelling scaffolds were implanted: one group without the DBA monomer containing a hydrolyzable lactone ring for LCST modulation (15 wt % TGM), and two groups with the DBA monomer at different polymer wt % concentrations (15 and 20 wt % TGM/DBA). MicroCT was used for nondestructive, quantitative analysis of bony bridging, union, and bone volume, as well as 3D visualization of the extent and spatial distribution of mineralization. For bony bridging of the defects, maximum intensity projections (MIPs) were generated from each of the microCT datasets and scored by three blinded reviewers using the 0-4 grading scale detailed in Table 4. FIG. 43 provides respective examples of actual MIPs for each score (A=4; B=3; C=2; D=1). FIG. 37 shows the results from the scoring at 4 and 12 weeks. At the 4 week timepoint, the average union microCT score for 15 wt % TGM, 15 wt % TGM/DBA, and 20 wt % TGM/DBA was ~2, indicating that bony bridging is only observed at the defect borders. At the 12 week timepoint, the 15 wt % TGM and 20 wt % TGM/DBA demonstrated an increase in bony bridging, leading to a statistically significant increase in the average union microCT score compared to the 4 week timepoint.

TABLE 4

Scoring guide for bony bridging and union in microCT datasets

| Description | Score |
|---|---|
| Bony bridging over entire defect span at longest point | 4 |
| Bony bridging over partial length of defect | 3 |
| Bony bridging only at defect borders | 2 |
| Few bony spicules dispersed throughout defect | 1 |
| No bone formation within defect | 0 |

FIG. 38 shows the results from the quantification of bone volume using microCT. The data are reported as the % binarized object volume within a given VOI above a critical threshold grayscale value of 70, and include mineralization within the implant and bone formation across the defect. Both the 15 wt % TGM and 20 wt % TGM/DBA groups demonstrated a significant increase in the bone volume from 4 to 12 weeks. Additionally, the bone volume of the 15 wt % TGM group was significantly higher at 12 weeks compared to the two other groups.

To examine the spatial distribution and nature of mineralization in detail, 3D models of each sample were generated via microCT using the critical threshold value. Two representative samples in the 15 wt % TGM and 20 wt % TGM groups demonstrating the most mineralization at 12 weeks are shown in FIG. 39. Bone regeneration across the defect at 12 weeks primarily extended underneath the hydrogel for both groups. Mineralization additionally occurred throughout the hydrogel for the 15 wt % TGM group. This is in contrast to other samples, which showed bone formation at the defect borders, or, as demonstrated by the representative 4 week sample in FIG. 39, mineralization as nodules above the hydrogel.

Descriptive Light Microscopy

The samples were grossly examined after histological staining with hematoxylin & eosin (H&E), von Kossa, and Goldner's trichrome, and representative images from each group and time point are shown in FIG. 40. For all sections, the implants were visible, although shrinkage and delamination artifacts generally associated with hydrogel histology were observed in many samples. For both the 4 and 12 week samples, a thin fibrous capsule was observed around the hydrogel, particularly around the periosteal border. At 4 weeks, the tissue at the hydrogel-defect interface was generally loose and fibrous in nature and minimal bone formation was observed. The inflammatory response, characterized by the presence of neutrophils and macrophages, was also minimal and occurred primarily at the periosteal border. At 12 weeks, the inflammatory response was generally mitigated and the tissue at the hydrogel-defect interface was more organized, as shown by the high-magnification subsets in FIG. 40. Although all the hydrogels did not demonstrate measurable scaffold fragmentation, instances of cell-mediated bone formation across the defect were more pronounced in the 15 wt % TGM group compared to the other groups. With H&E and Goldner's trichrome staining, cell-mediated bone formation was generally observed on the dural side of the defect, although in certain 15 wt % TGM samples, significant mineralization was also seen throughout the center of the hydrogel with von Kossa staining. Additionally, promising direct bone-implant contact was observed in several of the 15 wt % TGM samples at 12 weeks, a representative example of which is shown in FIG. 40 (panel F) and the high-magnification subsets. With the coronal cross sectional slices, no significant amounts of hydrogel mineralization within the implant or cell-mediated bone formation across the dural side of the defect were observed.

Quantitative Histological Analysis

Samples were evaluated for bony bridging across the defect and mineralization of the scaffold as shown in FIG. 42A-B according to the inlaid scoring rubrics. FIG. 42A shows the scoring results for mineralization within the scaffold. The average score for the 15 wt % TGM group at 4 and 12 weeks was higher than that of the 15 wt % TGM/DBA and 20 wt % TGM/DBA groups, but not significantly. FIG. 42B shows the scoring results for bony bridging across the central coronal cross-section of the scaffold along the dural side of the implant. The 15 wt % TGM group showed significantly increased scores in bony bridging from 4 to 12 weeks, but the scores were only significant from the 15 wt % TGM/DBA group at 12 weeks. The overall tissue response was also scored (Table 6), with only the 20 wt % TGM group showing a significant difference between the 4 and 12 week timepoints.

TABLE 6

Histological scoring guide and scores for overall tissue response

Overall Tissue Response

| Description | Score |
| --- | --- |
| Direct bone to implant contact without soft interlayer | 4 |
| Remodeling lacuna with osteoblasts and/or osteoclasts at surface | 3 |
| Majority of implant is surrounded by fibrous tissue capsule | 2 |
| Unorganized fibrous tissue (majority of tissue is not arranged as capsule) | 1 |
| Inflammation marked by an abundance of inflammatory cells and poorly organized tissue | 0 |

| Group | Timepoint (weeks) | Average Histological Score |
| --- | --- | --- |
| 15 wt % TGM | 4 | 0.14 ± 0.4 |
| | 12 | 0.83 ± 1.2 |
| 15 wt % TGM/DBA | 4 | 0.29 ± 0.5 |
| | 12 | 0.86 ± 0.7 |
| 20 wt % TGM/DBA | 4 | 0.00 ± 0.0 |
| | 12 | 0.83 ± 0.8* |

*significant difference between the 4 and 12 week timepoint (p < 0.05)

In Vitro Acellular Mineralization

To investigate the mechanism behind hydrogel mineralization, an acellular in vitro study was performed by culturing the hydrogels in four solutions: PBS pH 7.4 (PBS), SBF 1× (SBF), complete osteogenic media without serum (NS), and complete osteogenic media with serum (S). FIG. 41 shows the calcium content of the hydrogels over the 28 day culture period. All of the groups demonstrated significantly increased calcium content over time after culture in complete osteogenic media with serum. This corresponded with increased von Kossa histological staining of hydrogel cross-sections over time for all groups, which detects the presence of phosphate groups (data not shown). However, the amount of calcium in the 15 wt % TGM group was significantly larger than that of the 15 wt % and 20 wt % TGM/DBA groups at the 7, 14 and 28 day timepoints. The 15 wt % TGM group also displayed significantly increased calcium content in the SBF 1× and complete osteogenic media without serum (NS) conditions; however, these values were not statistically different from the calcium content of complete osteogenic media with serum (S) conditions.

Conclusion:

This Example evaluated the mineralization capacity, bone formation capability, and tissue response of acellular PNiPAAm-based hydrogels in an 8 mm critical size rat cranial defect. Although minimal bone formation and hydrogel mineralization was observed at 4 weeks for all groups, significantly higher bone formation across the defect and mineralization within the implant was observed for the 15 wt % TGM and 20 wt % TGM/DBA groups after 12 weeks. The results, coupled with an in vitro acellular mineralization study, suggest that these hydrogels undergo matrix hydrophobicity-dependent mineralization, which is accelerated by the adsorption of calcium-binding and nucleating proteins on hydrophobic hydrogel surfaces. These mineralizable and biocompatible injectable hydrogels possess great potential as acellular strategies or stem cell carriers for craniofacial tissue engineering applications.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present disclosure. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

REFERENCES

Klouda L, Perkins K R, Watson B M, et al. Thermoresponsive, In Situ Cross-linkable Hydrogels Based on Nisopropylacrylamide: Fabrication, Characterization and Mesenchymal Stem Cell Encapsulation. Acta Biomaterialia. 2011; 7:1460-1467.

Cui Z, Lee B H, Pauken C, Vernon B. Manipulating Degradation Time in a NIPAAM-Based Copolymer with Hydrolysis-Dependent LCST. Journal of Biomaterials Science Polymer Edition. 2010; 21 (6):913-926.

Dey R K, Ray A R. Synthesis, Characterization and Blood Compatibility of Copolymers Derived from Polyamidoamines and Vinyl Acetate. Journal of Macromolecular Science, Part A: Pure and Applied Chemistry. 2005; 42:351-364.

Ferruti P, et al. Poly(amido-amine)s: Biomedical Applications. Macromol. Rapid Commun 2002; 23:332-355.

Hacker M C, et al. Synthesis and Characterization of Injectable, Thermally and Chemically Gelable, Amphiphilic p(Nisopropylacrylamide)-Based Macromers. Biomacromolecules. 2008; 9:1558-1570.

Klouda et al., Biomaterials (2009)

Cui et al., Biomacromolecules (2007)

Gutowska, A.; Jeong, B.; Jasionowski, M. *Anat. Rec.* 2001, 263, 342-349.

Temenoff, J. S.; Mikos, A. G. *Biomaterials* 2000, 21, 2405-2412.

Kretlow, J. D.; Klouda, L.; Mikos, A. G. *Adv. Drug Del. Rev.* 2007, 59, 263-273.

Kretlow, J. D.; Young, S.; Klouda, L.; Wong, M.; Mikos, A. G. *Adv. Mater.* 2009, 21, 3368-3393.

Klouda, L.; Mikos, A. G. *Eur. J. Pharm. Biopharm.* 2008, 68, 34-45.

Hacker, M. C.; Klouda, L.; Ma, B. B.; Kretlow, J. D.; Mikos, A. G. *Biomacromolecules* 2008, 9, 1558-1570.

Emik, S.; Gurdag, G. *J. Appl. Polym. Sci.* 2006, 100, 428-438.

Guan, J. J.; Hong, Y.; Ma, Z. W.; Wagner, W. R. *Biomacromolecules* 2008, 9, 1283-1292.

Ma, Z. W.; Nelson, D. M.; Hong, Y.; Wagner, W. R. *Biomacromolecules* 2010, 11, 1873-1881.

Cui, Z. W.; Lee, B. H.; Pauken, C.; Vernon, B. L. *J. Biomater. Sci., Polym. Ed.* 2010, 21, 913-926.

Klouda, L.; Hacker, M. C.; Kretlow, J. D.; Mikos, A. G. *Biomaterials* 2009, 30, 4558-4566.

Klouda, L.; Perkins, K. R.; Watson, B. M.; Hacker, M. C.; Bryant, S. J.; Raphael, R. M.; Kasper, F. K.; Mikos, A. G. *Acta Biomater.* 2011, 7, 1460-1467.

Li, Z. Q.; Guo, X. L.; Matsushita, S.; Guan, J. J. *Biomaterials* 2011, 32, 3220-3232.

Cui, Z. W.; Lee, B. H.; Pauken, C.; Vernon, B. L. *J. Biomed. Mater. Res., Part A* 2011, 98A, 159-166.

Fujimoto, K. L.; Ma, Z. W.; Nelson, D. M.; Hashizume, R.; Guan, J. J.; Tobita, K.; Wagner, W. R. *Biomaterials* 2009, 30, 4357-4368.

Robb, S. A.; Lee, B. H.; McLemore, R.; Vernon, B. L. *Biomacromolecules* 2007, 8, 2294-2300.

Kretlow, J. D.; Hacker, M. C.; Klouda, L.; Ma, B. B.; Mikos, A. G. *Biomacromolecules* 2010, 11, 797-805.

Cellesi, F.; Tirelli, N.; Hubbell, J. A. *Macromol. Chem. Phys.* 2002, 203, 1466-1472.

Cellesi, F.; Tirelli, N.; Hubbell, J. A. *Biomaterials* 2004, 25, 5115-5124.

Lee, B. H.; West, B.; McLemore, R.; Pauken, C.; Vernon, B. L. *Biomacromolecules* 2006, 7, 2059-2064.

Wang, Z. C.; Xu, X. D.; Chen, C. S.; Yun, L.; Song, J. C.; Zhang, X. Z.; Zhuo, R. X. *ACS Appl. Mater. Interfaces* 2010, 2, 1009-1018.

Cheng, V.; Lee, B. H.; Pauken, C.; Vernon, B. L. *J. Appl. Polym. Sci.* 2007, 106, 1201-1207.

Mizuntani, M.; Satoh, K.; Kamigaito, M. *Macromolecules* 2011, 44, 2382-2386.

Wei, H. L.; Yang, Z.; Chu, H. J.; Zhu, J.; Li, Z. C.; Cui, J. S. *Polymer* 2010, 51, 1694-1702.

Wang, Z. C.; Xu, X. D.; Chen, C. S.; Wang, G. R.; Cheng, S. X.; Zhang, X. Z.; Zhuo, R. X. *React. Funct. Polym.* 2009, 69, 14-19.
Ferruti, P.; Marchisio, M. A.; Duncan, R. *Macromol. Rapid Commun.* 2002, 23, 332-355.
Lin, C.; Zhong, Z. Y.; Lok, M. C.; Jiang, X. L.; Hennink, W. E.; Feijen, J.; Engbersen, J. F. J. *Bioconjugate Chem.* 2007, 18, 138-145.
Magnaghi, V.; Conte, V.; Procacci, P.; Pivato, G.; Cortese, P.; Cavalli, E.; Pajardi, G.; Ranucci, E.; Fenili, F.; Manfredi, A.; Ferruti, P. *J. Biomed. Mater. Res., Part A* 2011, 98A, 19-30.
Navath, R. S.; Menjoge, A. R.; Dai, H.; Romero, R.; Kannan, S.; Kannan, R. M. *Mol. Pharm.* 2011, 8, 1209-1223.
Dey, R. K.; Ray, A. R. *J. Macromol. Sci., Part A: Pure Appl. Chem.* 2005, A42, 351-364.
Jain, R.; Standley, S. M.; Frechet, J. M. J. *Macromolecules* 2007, 40, 452-457.
Ferruti, P.; Ranucci, E.; Sartore, L.; Bignotti, F.; Marchisio, M. A.; Bianciardi, P.; Veronese, F. M. *Biomaterials* 1994, 15, 1235-1241.
Ferruti, P.; Manzoni, S.; Richardson, S. C. W.; Duncan, R.; Pattrick, N. G.; Mendichi, R.; Casolaro, M. *Macromolecules* 2000, 33, 7793-7800.
Timmer, M. D.; Shin, H.; Horch, R. A.; Ambrose, C. G.; Mikos, A. G. *Biomacromolecules* 2003, 4, 1026-1033.
Lynn, D. M.; Langer, R. *J Am. Chem. Soc.* 2000, 122, 10761-10768.
Klouda L. Acta *Biomaterialia*. 2011; 7:1460-1467.
Ekenseair A K. *Biomacromolecules*. 2012; 13 (6):1908-1915.
Cui Z. *J Biomater Sci Polym Ed.* 2010; 21 (6):913-926.
Klouda L. *Biomaterials*. 2009; 30:4558-4566.
Spicer P. *Nature Protocols*. 2012; 7:1918-1929.

What is claimed is:

1. A composition comprising a poly(N-isopropylacrylamide)-based macromer and a diamine-based macromer, wherein the poly(N-isopropylacrylamide)-based macromer has a polymer backbone comprising glycidyl methacrylate (GMA) and N-isopropylacrylamide (NiPAAm), and wherein the poly(N-isopropylacrylamide)-based macromer is cross-linked by the diamine-based macromer via the GMA of the poly(N-isopropylacrylamide)-based macromer and an amine functional group of the diamine-based macromer.

2. The composition of claim 1 wherein the poly(N-isopropylacrylamide)-based macromer is selected from the group consisting of p(NiPAAm-co-GMA), p(NiPAAm-co-GMA-co-DBA-co-AA), and p(NiPAAm-co-GMA-co-AAm).

3. The composition of claim 1 wherein the diamine-based macromer is a polyamidoamine macromer.

4. The composition of claim 3 wherein the polyamidoamine macromer comprises bisacrylamide.

5. The composition of claim 1 wherein the diamine-based macromer increases hydrophilicity of the composition.

6. The composition of claim 1 wherein the composition is liquid.

7. The composition of claim 1 further comprising mesenchymal stem cells.

8. The composition of claim 1 further comprising growth factors.

9. The composition of claim 1 further comprising mesenchymal stem cells and growth factors.

10. A method comprising:
combining a poly(N-isopropylacrylamide)-based macromer with a diamine-based macromer to form a composition, wherein the poly(N-isopropylacrylamide)-based macromer has a polymer backbone comprising glycidyl methacrylate (GMA) and N-isopropylacrylamide (NiPAAm); and
injecting the composition into a defect in a mammal immediately following combining the poly(N-isopropylacrylamide)-based macromer with a diamine-based macromer.

11. The method of claim 10 wherein the defect is a craniofacial defect.

12. The method of claim 10 wherein the poly(N-isopropylacrylamide) macromer is selected from the group consisting of p(NiPAAm-co-GMA), p(NiPAAm-co-GMA-co-DBA-co-AA), and p(NiPAAm-co-GMA-co-AAm).

13. The method of claim 10 wherein the wherein the diamine-based macromer is a polyamidoamine macromer.

14. The method of claim 13 wherein the polyamidoamine macromer comprises bisacrylamide.

15. The method of claim 10 wherein the composition does not impede tissue formation within the defect.

16. The method of claim 10 wherein the diamine-based macromer increases hydrophilicity of the composition and mitigates syneresis.

* * * * *